US009810692B2

(12) United States Patent
Hannani et al.

(10) Patent No.: US 9,810,692 B2
(45) Date of Patent: Nov. 7, 2017

(54) METHODS FOR PREDICTING THE SENSITIVITY OF A SUBJECT TO IMMUNOTHERAPY

(71) Applicant: INSTITUT GUSTAVE ROUSSY, Villejuif (FR)

(72) Inventors: Dalil Hannani, Villejuif (FR); Laurence Zitvogel, Paris (FR); Caroline Robert, Fontenay-aux-Roses (FR); Nathalie Chaput-Gras, Paris (FR)

(73) Assignee: INSTITUT GUSTAVE ROUSSY, Villejuif (FR)

( * ) Notice: Subject to any disclaimer, the term of this patent is extended or adjusted under 35 U.S.C. 154(b) by 0 days.

(21) Appl. No.: 14/438,275

(22) PCT Filed: Oct. 25, 2013

(86) PCT No.: PCT/EP2013/072367
§ 371 (c)(1),
(2) Date: Apr. 24, 2015

(87) PCT Pub. No.: WO2014/064240
PCT Pub. Date: May 1, 2014

(65) Prior Publication Data
US 2015/0268243 A1    Sep. 24, 2015

Related U.S. Application Data

(60) Provisional application No. 61/718,771, filed on Oct. 26, 2012.

(30) Foreign Application Priority Data

Oct. 26, 2012  (EP) .................................. 12306329

(51) Int. Cl.
*G01N 33/574* (2006.01)
*A61K 39/395* (2006.01)
*A61K 39/00* (2006.01)

(52) U.S. Cl.
CPC ............................ *G01N 33/57488* (2013.01); *A61K 39/39541* (2013.01); *G01N 33/5743* (2013.01); *G01N 33/57484* (2013.01); *A61K 2039/5158* (2013.01); *G01N 2333/7155* (2013.01); *G01N 2333/904* (2013.01); *G01N 2800/52* (2013.01)

(58) Field of Classification Search
None
See application file for complete search history.

(56) References Cited

U.S. PATENT DOCUMENTS

| 4,876,191 A * | 10/1989 | Hollander .............. C07K 16/40 435/174 |
| 5,292,636 A * | 3/1994 | Kung .................. C07K 16/2812 435/34 |
| 6,258,540 B1 * | 7/2001 | Lo ........................ C12Q 1/6879 435/440 |
| 6,355,623 B2 * | 3/2002 | Seidman ................ A61K 31/52 514/263.4 |
| 2015/0079100 A1 * | 3/2015 | Roy .................... C07K 16/2818 424/142.1 |
| 2015/0283234 A1 * | 10/2015 | Graziano ........... C07K 16/2803 424/139.1 |

OTHER PUBLICATIONS

Bogner et al. (J. Immunotherapy, 1992 11:111-118).*
Bien and Balcerska (Biomarkers Feb. 2008 13(1): 1-26).*
LDH/eClinpath (Cornell Univ. College of Vet Med. http://www.eclinpath.com/chemistry/muscle/lactate-dehydrogenase/ downloaded Mar. 11, 2017).*
Brusko, T.M., et al., "Influence of Membrane CD25 Stability on T Lymphocyte Activity: Implications for Immunoregulation," *PLoS One*, Nov. 2009, pp. 1-13, vol. 4, No. 11, Document No. e7980.
Khan, S., et al., "Tremelimumab (anti-CTLA4) mediates immune responses mainly by direct activation of T effector cells rather than by affecting T regulatory cells," *Clinical Immunology*, 2011, pp. 85-96, vol. 138.
Mellman, I., et al., "Cancer immunotherapy comes of age," *Nature*, Dec. 22-29, 2011, pp. 480-489, vol. 480.
Menard, C., et al., "CTLA-4 Blockade Confers Lymphocyte Resistance to Regulatory T-Cells in Advanced Melanoma: Surrogate Marker of Efficacy of Tremelimumab?," *Clinical Cancer Research*, Aug. 15, 2008, pp. 5242-5249, vol. 14, No. 16.
Written Opinion in International Application No. PCT/EP2013/072367, dated Feb. 4, 2014, pp. 1-10.

* cited by examiner

*Primary Examiner* — Peter J Reddig
(74) *Attorney, Agent, or Firm* — Saliwanchik, LLoyd & Eisenschenk

(57) ABSTRACT

The present invention relates to a method of assessing, predicting or monitoring the sensitivity of a subject having a tumor or cancer to an immunotherapeutic molecule acting on the subject's T cells, to a method of selecting an appropriate treatment of cancer, to a method of screening or identifying a compound suitable for improving the treatment of a cancer, and to the use of corresponding kits. The method of predicting or monitoring the sensitivity of a subject having a tumor to an immunotherapeutic molecule acting on the subject's T cells typically comprises a step a) of determining, in a biological sample from said subject, the expression level of soluble CD25 (sCD25) and, when the expression level is determined, a step b) of comparing at least said expression level to a reference expression level, thereby assessing whether the subject having a tumor is responsive or resistant to the immunotherapeutic molecule.

12 Claims, 27 Drawing Sheets

METHODS FOR PREDICTING THE SENSITIVITY OF A SUBJECT TO IMMUNOTHERAPY

CROSS-REFERENCE TO RELATED APPLICATIONS

This application is the U.S. national stage application of International Patent Application No. PCT/EP2013/072367, filed Oct. 25, 2013, which claims the benefit of U.S. Provisional Patent Application No. 61/718,771, filed Oct. 26, 2012.

FIELD OF THE INVENTION

The present invention relates to a method of assessing, predicting or monitoring the sensitivity of a subject having a tumor or cancer to an immunotherapeutic molecule acting on the subject's T cells, to a method of selecting an appropriate treatment of cancer, to a method of screening or identifying a compound suitable for improving the treatment of a cancer, and to the use of corresponding kits. The method of predicting or monitoring the sensitivity of a subject having a tumor to an immunotherapeutic molecule acting on the subject's T cells typically comprises a step a) of determining, in a biological sample from said subject, the expression level of soluble CD25 (sCD25) and, when the expression level is determined, a step b) of comparing at least said expression level to a reference expression level, thereby assessing whether the subject having a tumor is responsive or resistant to the immunotherapeutic molecule.

The method may further comprise a step a') of determining, in a biological sample from the subject, the expression level of lactic acid dehydrogenase (LDH) and, when the LDH expression level is determined, a step b') of comparing said LDH expression level to a reference expression level.

BACKGROUND OF THE INVENTION

Melanoma is less common than other skin cancers. However, it is much more dangerous if it is not found early. It causes the majority (75%) of deaths related to skin cancer. Worldwide, doctors diagnose about 160,000 new cases of melanoma yearly. It is more common in women than in men. It is particularly common among Caucasians, especially northwestern Europeans living in sunny climates. There are high rates of incidence in Oceania, Northern America, Europe, southern Africa, and Latin America, with a paradoxical decrease in southern Italy and Sicily. This geographic pattern reflects the primary cause, ultraviolet light (UV) exposure crossed with the amount of skin pigmentation in the population. According to a WHO report, about 48,000 melanoma-related deaths occur worldwide per year (Lucas et al., 2006, Environmental Burden of Disease Series. 13. World Health Organization). The treatment includes surgical removal of the tumor. If melanoma is found early, while it is still small and thin, and if it is completely removed, then the chance of cure is high. The likelihood of the melanoma coming back or spreading depends on how deeply it has gone into the layers of the skin. For melanomas that come back or spread, treatments include chemo- and immunotherapy or radiation therapy.

Metastatic melanoma is a poor-prognosis disease. This cancer has the steepest incidence rate worldwide and considering skin cancers, it is the first cause of mortality with up to 12,200 deaths expected in 2012 (American Cancer Society, 2008, Cancer Facts and Figures). The five-year survival rate is 5-10 percent and the median survival is 6 to 10 months (Balch et al., 2009, J Clin Oncol; Tsao et al., 2004, N Engl J Med). Until the recent development of new drugs such as immunotherapy and anti-BRAF targeted agents, no therapy had been able to demonstrate any significant overall survival benefit in patients with metastatic melanoma (Hodi et al., 2010, N Engl J Med; Chapman et al., 2001, N Engl J Med).

Ipilimumab (Yervoy®) and Tremelimumab are monoclonal antibodies directed against cytotoxic T-lymphocyte-associated antigen 4. These fully human antibodies (IgG1κ) downregulate an inhibitory pathway of T lymphocytes, and potentiate the immune response against melanoma cells (Kaehler et al., 2010, Semin Oncol). Ipilimumab in particular improves overall survival in patients with pretreated metastatic melanoma (Hodi et al., 2010, N Engl J Med). In this phase III randomized trial the median overall survival was 10.1 months in the Ipilimumab group (at the dose of 3 mg/kg), versus 6.4 months in the gp 100 group. Robert et al. showed in another randomized phase III trial that Ipilimumab at the dose of 10 mg/kg, in combination with dacarbazine, was associated with a longer overall survival than dacarbazine alone (11.2 months versus 9.2 months respectively) in previously untreated metastatic melanoma patients (Robert et al., 2011, N Engl J Med). These studies led to the approval of Ipilimumab by the Food and Drug Administration (FDA) and by the European Medicines Agency (EMA) as a second-line treatment of metastatic melanoma.

The issues encountered during clinical trials are noteworthy. First, the safety profile is unusual with new autoinflammatory side effects called immune-related adverse events (irAEs) (Weber et al., 2009, Cancer Immunol Immunother). The cutaneous and gastrointestinal irAEs are frequent, respectively 40% and 30% of patients, and can be life-threatening (Di Giacomo et al., 2010, Semin Oncol). Hodi et al. reported 12% of grade 3-4 severe colitis and 14 drug-related deaths (2.1%) in 643 patients receiving Ipilimumab (Hodi et al., 2010, N Engl J Med). The irAEs are dose-dependent, are usually manageable with high-dose corticosteroids and might, in severe and steroid-resistant cases, require more potent immunosuppressive drugs like anti-TNF-α (Wolchock et al., 2010, Lancet Oncol; Weber et al., 2012, J Clin Oncol). Secondly, patterns of response to Ipilimumab are different from those to cytotoxic agents. New criteria of evaluation have been developed to replace the Response Evaluation Criteria in Solid Tumors (RECIST, WHO Criteria) that are more adapted to immunotherapeutic agents or molecules. Indeed, Ipilimumab and other immunotherapeutic agents, like anti-programmed death-1 (anti-PD-1) monoclonal antibodies, are now commonly evaluated using the so-called "immune-related response criteria" (Wolchock et al., 2009, Clin Cancer Res). Thus, initial increase in tumor burden and delayed clinical response are new profiles that may not require discontinuation of Ipilimumab.

While about 15-20% of patients are long-term responders, the clinical use of Ipilimumab is currently hampered by two main problems: i) side effects as explained previously (indeed, up to 30% patients develop adverse immune related side effects, such as diarrhea, colitis, hypophysitis, skin erythroderma, fatigue and three case reports of agranulocytosis, etc., sometimes steroid-resistant and precluding the continuation of the treatment); and ii) the cost of the therapy which is 94,000 dollars/4 injections (while a responder needs more than a year of therapy administered every 3 weeks up to stabilization or cure and then every 2 months as a maintenance therapy). So far, the lymphocyte counts, the eosinophile counts and/or the percentages of Inducible T Cell Costimulator (ICOS) expressing CD4+ T cells after one or two cycles of therapy appear to indicate responders from non-responders. However, none of these above-quoted markers represent a biomarker of high specificity and positive predictive value. Hence, there is an unmet medical need for an efficient predictive marker of response and/or toxicity, which would decrease the percentage of cancer patients suffering from immune-related adverse events but failing to respond to the selected anti-cancer drug(s), or worse being further affected or poisoned by the selected anti-cancer drug(s).

SUMMARY OF THE INVENTION

The inventors now identify novel biomarkers of response to immunotherapeutic molecules acting on the patient's T cells. These biomarkers, namely soluble CD25 (sCD25) and/or lactic acid dehydrogenase (lactate dehydrogenase, LDH), advantageously allow an increase of the detection of responders from 1/10 (using markers of the art) to 1/3 (using the herein-described biomarkers) and the method of the invention using any one of these new biomarkers allows a false negative rate of 0% and has a negative predictive value of 100%. In other words, patients who will not respond to the treatment using the immunotherapeutic molecule will all be identified. In addition, both the sensitivity of the method and its specificity meet the medical community's expected needs as they are respectively of 100% and about 70%.

A first method herein described is an in vitro or ex vivo method of predicting (or assessing) or monitoring the sensitivity of a subject having a tumor to an immunotherapeutic molecule acting on the subject's T cells for treating the tumor, which method comprises a step a) of determining, in a biological sample from said subject, preferably selected from a blood, a serum, a plasma sample or a derivative thereof, the expression level of soluble CD25 (sCD25) and, when the sCD25 expression level is determined, a step b) of comparing said sCD25 expression level to a reference expression level, thereby assessing whether the subject having a tumor is sensitive or resistant to the immunotherapeutic molecule.

The method advantageously further comprise a step a') of determining, in a biological sample from the subject, preferably selected from a blood, a serum, a plasma sample or a derivative thereof, the expression level of lactic acid dehydrogenase (LDH) and, when the LDH expression level is determined, a step b') of comparing said LDH expression level to a reference expression level.

A particular method herein described is an in vitro or ex vivo method of selecting, for a subject having a tumor, a treatment comprising an immunotherapeutic molecule acting on the subject's T cells efficient against the tumor of a subject. This method preferably comprises the following steps:
  a step a) of determining the sCD25 basal expression level, in a biological sample of the subject having a tumor, before any administration to the subject of an immunotherapeutic molecule for treating the subject's tumor, typically before any administration to the subject of a therapeutic dose of the immunotherapeutic molecule;
  a step a') of determining, in a biological sample of the subject having a tumor, the sCD25 response expression level after the administration to said subject of at least one therapeutic dose of the immunotherapeutic molecule for treating the tumor;
  a step b) of comparing said sCD25 response expression level to said sCD25 basal expression level and to a reference expression level in a control population, a sCD25 response expression level identical to the sCD25 basal expression level or below the reference expression level being the indication that an immunotherapeutic molecule acting on the subject's T cells will not be efficient alone in the subject;
  and, if appropriate, a step c) of selecting an appropriate treatment of the subject's tumor combining said immunotherapeutic molecule with an additional compound selected from interleukin-2 (IL-2), IL-2 superkine, interleukin-15 (IL-15) and sushi IL-15.

On the contrary a sCD25 response expression level above both sCD25 basal expression level and sCD25 reference expression level being the indication that the immunotherapeutic molecule acting on the subject's T cells will be efficient as such against the tumor of the subject.

Also herein described is a method of identifying an inappropriate treatment of a tumor for a subject having a tumor, comprising preferably 1) applying the previously described method of selecting an immunotherapeutic molecule acting on the subject's T cells and in addition 2) applying, for a subject for whom the immunotherapeutic molecule is identified as being efficient as such against the subject's tumor, an additional step d) of determining, in a biological sample of said subject, the sCD25 response expression level after the administration to said subject of the second therapeutic dose of the immunotherapeutic molecule for treating the tumor, an increase of the sCD25 response expression level when compared to the sCD25 response expression level determined after the administration to said subject of the first therapeutic dose of the immunotherapeutic molecule for treating the tumor being the indication that the immunotherapeutic molecule is toxic for the subject and is an inappropriate treatment of a tumor for the subject.

Also herein described is a method for screening or identifying a compound suitable for improving the treatment of a tumor in a subject having a tumor, said method comprising determining the ability of a test compound to modify the expression of sCD25 or compensate for an abnormal expression thereof.

A further aspect relates to specific kits as well as their uses, in particular for assessing or monitoring the sensitivity of a subject having a tumor to an immunotherapeutic molecule acting on a subject's T cells selected from an anti-CTLA-4, anti-PD-1, anti-PDL-1, anti-PDL-2, anti-Tim3, anti-Lag3, anti-VISTA, anti-BTLA and anti-OX40 antibody. Such a kit comprises detection means selected from the group consisting of at least one antibody specific to sCD25, IL-2, sLAG3, IL-15, and/or sCD122; a molecule allowing detection of the antibody; at least one molecule allowing LDH detection; and, optionally, a leaflet providing the repective sCD25 IL-2, sLAG3, IL-15, sCD122 and/or LDH reference expression levels in control population(s).

DETAILED DESCRIPTION OF THE INVENTION

The inventors demonstrated in preclinical transplantable tumor models (MC38 colon cancer, MCA205 sarcoma) that the antitumor effects mediated by anti-CTLA4 antibody (Ab) markedly depend not only on CD4+ and CD8+ T cells, but also on the bioactivity of IL-2, IL-15, IL-2Rα chain (CD25) and IL-2Rβ chain (CD122). The present invention comes from the inventors' discovery that while anti-CTLA4

Ab (such as Ipilimumab, also identified as Yervoy®) or recombinant IL-2 (rIL-2), as a single agent, induces a significant but transient (anti-CTLA4 Ab) or no (rIL-2) control of tumor progression, on the contrary the combination of both IL-2, preferably rIL-2, and anti-CTLA4 antibody is markedly synergistic and surprisingly promotes long-term disease-free or stabilization of low tumor burdens.

As used herein, the "soluble CD25" (sCD25) is equivalent to soluble IL-2Rα chain and was first described in Rubin et al. (Rubin et al., 1985, J Immunol). An exemplary amino acid sequence is described in UniProtKB/Swiss-Prot database under accession number P01589.

The inventors analyzed the kinetics of serum levels of soluble CD25 (using two different ELISA kits), a surrogate marker of IL-2-induced T cell activation, during Ipilimumab treatment in five different cohorts: 1) metastatic melanoma (MM) treated with local radiotherapy+10 mg/kg Ipilimumab (N=7), 2) metastatic melanoma treated with Ipilimumab at a low dose (3 mg/kg) (N=10), 3) hormono-resistant prostatic cancer treated with radiotherapy+Ipilimumab (N=9), 4) metastatic melanoma (MM) treated with Ipilimumab at a low dose (3 mg/kg) (N=262), and 5) metastatic melanoma (MM) treated with Tremelimumab (15 mg/kg) (N=20).

They conclude to the efficacy of sCD25 as a biomarker allowing the identification of subjects having a cancer or tumor who will respond or not respond to an immunotherapeutic molecule acting on the subject's T cells or who will be further affected or poisoned by such an immunotherapeutic molecule. The immunotherapeutic molecule is typically an anti-CTLA4 antibody, in particular Ipilimumab or Tremelimumab. As explained in the experimental part, the inventors further established that the respective serum levels of LDH and sCD25 represent valuable predictors of resistance to Ipilimumab or Tremelimumab.

In the present invention, the cancer is a cancer that is usually or conventionally treated with one of the following therapies: a chemotherapy, a radiotherapy, an immunotherapy, in particular an antibody-based therapy (in particular an anti-CTLA4 antibody-based therapy), a hormonotherapy and a surgery.

The cancer or tumor may be any kind of cancer or neoplasia. The cancer is typically selected from a carcinoma, a sarcoma, a lymphoma, a melanoma, a pediatric tumor (such as neuroblastomas, ALK (anaplastic lymphoma kinase) lymphomas, osteosarcomas, medulloblastomas, glioblastomas, ependymomas, acute myeloid leukemia, and acute lymphoblastic leukemia) and a leukemia (also herein identified as "leukemia tumor"). The cancer is preferably selected from a melanoma, in particular an unresectable or metastatic melanoma ("MM"), preferably a melanoma that does not harbor a BRAF mutation; a prostate cancer, in particular a hormonotherapy-resistant prostate cancer or a metastatic prostate cancer (for example a prostate cancer with bone metastases); a lung cancer; a renal cell carcinoma tumor; and a colon cancer.

In the context of a conventional radiotherapy, the treatment may consist of exposing the subject to irradiation selected for example from XR, gamma irradiation and/or UVC irradiation.

Cancers sensitive to an immunotherapy are conventionally treated using a compound selected for example from IL-2 (Interleukine-2), IFN (Interferon) alpha (IFNa), and a vaccine.

Cancers sensitive to an antibody-based therapy, preferably to a monoclonal antibody-based therapy, are conventionally treated using a specific antibody (Ab) such as an anti-CTLA4 Ab (in particular Ipilimumab or Tremelimumab), anti-CD20 (pan B-Cell antigen) Ab, anti-Her2/Neu (Human Epidermal Growth Factor Receptor-2/NEU) Ab, anti-CD20, anti-EGFR, anti-PD-1 (Programmed cell death protein 1) Ab, an anti-PDL-1 (Programmed cell death protein ligand 1) Ab, an anti-PDL2 (Programmed cell death protein ligand 2) Ab, anti-Tim3 (T cell immunoglobulin-3) Ab, anti-Lag3 (Lymphocyte activation gene 3) Ab, anti-BTLA Ab, anti-VISTA Ab, and/or anti-CSF1R Ab.

Other immunotherapies comprise compounds leading to apoptosis such as Fas ligands or soluble/membrane bound TRAIL (TNF-related apoptosis-inducing ligand) or soluble/membrane bound TNF (tumor necrosis factor) alpha (TNFa).

Cancers sensitive to a hormonotherapy are conventionally treated using a compound such as an antiaromatase.

When the treatment is chemotherapy, this treatment may use a chemotherapeutic drug or agent, a cytotoxic agent or a cell death inducer, in particular a genotoxic agent. In a particular embodiment of the present invention, the chemotherapeutic agent is an agent selected for example from an anthracycline (DX, daunorubicin, idarubicin and MTX), an antimitotic agent (spindle poison such as vincristine or vinblastine), a DNA intercalating agent, a taxane (such as docetaxel, larotaxel, cabazitaxel, paclitaxel (PG-paclitaxel and DHA-paclitaxel), ortataxel, tesetaxel, and taxoprexin), gemcitabine, etoposide, mitomycin C, an alkylating agent (such as dacarbazine), a platin-based component such as CDDP and OXP, and a TLR (Toll-like receptor)-3 ligand.

In the context of the present invention, the patient or subject is a mammal. In a particular embodiment, the mammal is a human being, whatever its age or sex. The patient typically has a cancer or tumor. Unless otherwise specified in the present disclosure, the tumor is a cancerous or malignant tumor. Preferably the subject is a subject who has not been previously exposed to a treatment of cancer or a subject who has received the administration of at least one, possibly two or three, therapeutic dose(s) of a molecule or agent for treating the cancer or tumor, preferably of an immunotherapeutic molecule or agent.

In the context of melanoma cancer, a particular subpopulation of subjects is composed of subjects having or suffering from a metastatic melanoma, preferably a melanoma that does not harbor a BRAF mutation.

In the context of prostate cancer, a particular subpopulation of subjects is composed of subjects having hormonoresistant prostate cancer, typically together with bone metastases, in particular subjects treated with X-rays or taxanes and an anti-CTLA4 Ab.

Another particular subpopulation of subjects suffering from the herein-mentioned cancers is composed of subjects having a metastatic cancer (any kind of metastases) or for whom the tumor is unresectable.

Implementations of the methods of the invention involve obtaining a (biological) sample from a subject. The sample is preferably a fluid sample and may include serum, blood, plasma, lymphatic fluid, spinal fluid, pleural effusion, ascites, a derivative thereof, or a combination thereof. Cells are not included in the sample because these embodiments involve assaying for soluble, as opposed to cell-bound, biomarkers.

A method according to the present invention is an in vitro or ex vivo method of predicting (or assessing) or monitoring the sensitivity of a subject having a tumor to an immunotherapeutic molecule acting on the subject's T cells for treating the tumor, which method comprises a step a) of determining, in a biological sample from said subject, preferably selected from a blood, a serum, a plasma sample or a derivative thereof, the expression level(s) of at least one compound selected from soluble CD25 (sCD25), IL-2, IL-15, and sCD122, for example sCD25, IL-2, and IL-15, and/or the expression level of sCD122, and, when the corresponding expression level is determined, a step b) of comparing said expression level(s) to a reference expression level, thereby assessing or monitoring whether the subject having a tumor is sensitive (responsive) or resistant to the immunotherapeutic molecule.

In a particular embodiment, the sCD25, IL-2, IL-15 or sCD122 expression level determined in step a) is the sCD25, IL-2, IL-15 or sCD122 basal expression level in the subject, and step b) preferably further comprises comparing said basal expression level to an sCD25, IL-2, IL-15 or sCD122 response expression level in the subject determined after administration to said subject of the immunotherapeutic molecule.

In another particular embodiment, the method further comprises a step a') of determining, in a biological sample from said subject, preferably selected from a blood, a serum, a plasma sample or a derivative thereof, the expression level of lactic acid dehydrogenase (LDH) and, when the LDH basal expression level is determined, a step b') of comparing said LDH basal expression level to a reference expression level.

In a further particular embodiment, the sCD25, IL-2, IL-15 or sCD122 basal expression level(s), and optionally the LDH basal expression level, is/are determined before any administration to the subject of an immunotherapeutic molecule for treating the subject's tumor.

By "sensitivity" or "responsiveness" is intended herein the likelihood that a patient will respond to an immunotherapeutic treatment.

By "resistant" is intended herein the likelihood that a patient will not respond to an immunotherapeutic treatment.

Predictive methods of the invention can be used clinically to make treatment decisions by choosing as soon as possible the most appropriate treatment modalities for a particular patient.

In a particular embodiment, the immunotherapeutic molecule acting on the subject's T cells for treating the tumor is selected from an anti-CTLA-4, in particular an anti-CTLA-4 monoclonal antibody, preferably selected from Ipilimumab (Yervoy®) and Tremelimumab, and an anti-PD-1, anti-PDL-1, anti-PDL-2, anti-Tim3, anti-Lag3, anti-VISTA, anti-BTLA, and anti-OX40 monoclonal or polyclonal antibody.

If the subject is identified, using a method according to the present invention, as resistant to a particular treatment of cancer, the method advantageously further comprises a step of selecting a distinct or complementary therapeutic molecule, drug or composition, typically involving a "compensatory molecule", such as interleukin-2 (IL-2), interleukin-15 (IL-15), IL-2 superkine (Levin, Nature, 2012, 484:529-33), sushi IL-15, a nanobody or nanobodies, an immunocytokine, a modified antibody directed against T cell antigens, or a receptor coupled to a cytokine (see below), to be used in combination with the originally preselected immunotherapeutic drug or with a distinct therapeutic drug as the appropriate therapeutic treatment of cancer for the subject.

Preferably, the step of determining the basal expression level(s) of at least one of sCD25, IL-2, IL-15, sLAG3 and sCD122, and optionally the basal expression level of LDH, in a biological sample of the subject is performed before any administration to the subject of a therapeutic dose of the immunotherapeutic molecule preliminary selected for treating cancer. Preferably, the step of determining the response expression level of at least one of sCD25, IL-2, IL-15, sLAG3 and sCD122, and optionally the response expression level of LDH, in a biological sample of the subject is performed after administration to the subject of at least one therapeutic dose of the immunotherapeutic molecule. The expression "therapeutic dose" refers to the dose typically administered in a classical cancer treatment protocol by physicians. For example, and for human beings, in the context of metastatic melanoma, the protocol comprises an intravenous administration of Ipilimumab over 90 minutes at the therapeutic dose of 3 or 10 mg/Kg of body weight every three weeks, and in the context of a metastatic hormonoresistant prostate cancer, the protocol comprises an intravenous administration of Ipilimumab over 90 minutes at the dose of 3 or 10 mg/Kg of body weight every three weeks.

Less preferably but also possibly, this step of determining the response expression level of the herein-described biomarkers can be performed after the administration of a second immunotherapeutic dose to the subject.

In a particular embodiment, the method according to the present invention is an in vivo, in vitro or ex vivo method of predicting or monitoring the sensitivity of a subject having a cancer as herein described, for example a melanoma, a prostate cancer, a kidney cancer, a breast cancer or a colon cancer, preferably a metastatic melanoma, and the immunotherapy is selected from Ipilimumab, Tremelimumab and a combination thereof.

Herein described is a method comprising a step a) of determining the sCD25, IL-2, IL-15, and/or sCD122 basal expression level(s), and optionally the LDH basal expression level, in a biological sample of the subject having a tumor, before any administration to the subject of any therapeutic dose of the immunotherapeutic molecule for treating the subject's tumor, a step a') of determining, in a biological sample of said subject having a tumor, the sCD25, IL-2, IL-15, and/or sCD122 response expression level(s), and optionally the LDH response expression level, after the administration to said subject of at least one therapeutic dose of the immunotherapeutic molecule for treating the tumor, and a step b) of comparing said response expression level to said basal expression level and to a reference expression level in a control population, a response expression level above both the basal expression level and the reference expression level, preferably a 1.5-fold increase of said response expression level when compared to the basal expression level, being indicative of the sensitivity of the subject to the immunotherapeutic molecule as herein described.

Also herein described is a method comprising a step a) of determining the sCD25, IL-2, IL-15, and/or sCD122 basal expression level(s), and optionally the LDH basal response expression level, in a biological sample of the subject having a tumor, before any administration to the subject of any therapeutic dose of the immunotherapeutic molecule for treating the subject's tumor, a step a') of determining, in a biological sample of said subject having a tumor, the sCD25, IL-2, IL-15, and/or sCD122 response expression level(s), and optionally the LDH response expression level, after the administration to said subject of at least one therapeutic dose of the immunotherapeutic molecule for treating the tumor, and a step b) of comparing said response expression level to said basal expression level and to a reference expression level in a control population, a response expression level identical to the basal expression level or below the reference expression level being indicative of the resistance of the subject to the immunotherapeutic molecule.

Typically, the basal expression level is the level of the selected biomarker, i.e., the level of the sCD25, IL-2, IL-15, sLAG3 or sCD122 polypeptide, and optionally of the LDH polypeptide, in a subject's biological sample obtained from said subject before the administration of the first dose of immunotherapeutic molecule to said subject; the response expression level is the selected biomarker expression level in a subject's biological sample obtained from said subject after the administration of at least the first dose of immunotherapeutic molecule to said subject; and the "reference value" or "reference expression level" is the level of the selected biomarker in a control sample derived from one or more normal volunteers, and is typically the median value when obtained from the reference population. This reference value may vary, in particular for the sCD25 biomarker, depending on the subject's origin (typically Caucasian, Asian, Eurasian or African origin), on the cancer disease grade and on the selected kit.

As an example, when the patient is bearing a metastatic melanoma tumor, and the candidate immunotherapeutic drug (herein identified as immunotherapy) being an anti-CTLA-4 antibody, preferably selected from Ipilimumab (Yervoy®) and Tremelimumab, the reference expression level is for example about 900 pg/ml or about 80 pMol depending on the selected kit.

A typical reference expression level for LDH is about 500 IU.

In a particular method of the invention, the tumor is a melanoma and an sCD25 basal expression level above an sCD25 reference expression level is indicative of a resistance of the subject to the immunotherapeutic molecule and an sCD25 basal expression level below said sCD25 reference expression level is indicative of a sensitivity of the subject to the immunotherapeutic molecule.

Another particular method of the invention is an in vitro method of assessing the sensitivity of a subject having a metastatic melanoma to an immunotherapeutic molecule acting on the subject's T cells for treating the tumor. This method comprises a step of determining, in a biological sample from said subject, preferably selected from a blood, a serum, a plasma sample or a derivative thereof, the respective basal expression levels of soluble CD25 (sCD25) and LDH, and, when the sCD25 and LDH basal expression levels are determined, a step of comparing said sCD25 and LDH basal expression levels respectively to sCD25 and LDH reference expression levels, thereby assessing whether the subject having a tumor is sensitive or resistant to the immunotherapeutic molecule. In this method the LDH reference expression level is typically of about 500 IU and an sCD25 basal expression level above a sCD25 reference expression level together with an LDH basal expression level above said LDH reference expression level are indicative of a resistance of the subject to the immunotherapeutic molecule, an sCD25 basal expression level below said sCD25 reference expression level together with an LDH basal expression level below said LDH reference expression level being on the contrary indicative of a sensitivity of the subject to the immunotherapeutic molecule.

In another particular method of the invention, the method comprises a step a) of determining the sCD25 basal expression level, in a biological sample of the subject having a tumor, before any administration to the subject of an immunotherapeutic molecule for treating the subject's tumor, a step a') of determining, in a biological sample of the subject having a tumor, the sCD25 response expression level after the administration to said subject of at least one therapeutic dose of the immunotherapeutic molecule for treating the tumor, and a step b) of comparing said sCD25 response expression level to said sCD25 basal expression level and to a reference expression level in a control population, an sCD25 response expression level above both the sCD25 basal expression level and the reference expression level, preferably a 1.5-fold increase of said sCD25 response expression level when compared to the sCD25 basal expression level, being indicative of the sensitivity of the subject to the immunotherapeutic molecule.

A further particular method of the invention comprises a step a) of determining the sCD25 basal expression level, in a biological sample of the subject having a tumor, before any administration to the subject of an immunotherapeutic molecule for treating the subject's tumor, a step a') of determining, in a biological sample of the subject having a tumor, the sCD25 response expression level after the administration to said subject of at least one therapeutic dose of the immunotherapeutic molecule for treating the tumor, and a step b) of comparing said sCD25 response expression level to said sCD25 basal expression level and to a reference expression level in a control population, an sCD25 response expression level identical to the sCD25 basal expression level or below the reference expression level being indicative of a resistance of the subject to the immunotherapeutic molecule.

In some embodiments of the invention, identification of a soluble biomarker according to the present invention involves use of at least one polypeptide binding agent. Furthermore, it is contemplated that this polypeptide binding agent may or may not be specific to the soluble biomarker. For example, the polypeptide binding agent may bind to a part of the biomarker (e.g., an epitope) that is not available when the biomarker is bound to a cell. Alternatively, different conformations may serve as the basis for binding agents capable of distinguishing between soluble and bound biomarker.

The polypeptide is, in particular embodiments, an antibody. In further embodiments in relation to CD25 or LDH, the antibody is a monoclonal antibody. The antibody, in some embodiments, immunologically binds to more than one epitope from the same soluble CD25 or LDH polypeptide.

In particular the anti-CD25 antibody may be the clone 24204 mAb (R&D systems) or 11H2 mAb (Beckman Coulter). The antibody can be bi-specific, recognizing two different epitopes.

In some embodiments of the invention, the biomarker binding agent, in particular the the soluble biomarker binding agent, is an aptamer.

In some embodiments of the invention, the biomarker binding agent is labeled. In further embodiments, the label is radioactive, fluorescent, chemiluminescent, an enzyme, or a ligand. It is also specifically contemplated that a binding agent is unlabeled, but may be used in conjunction with a detection agent that is labeled. A detection agent is a compound that allows for the detection or isolation of itself so as to allow detection of another compound that binds, directly or indirectly. An indirect binding refers to binding among compounds that do not bind each other directly but associate or are in a complex with each other because they bind the same compounds or compounds that bind each other.

Other embodiments of the invention involve a second biomarker polypeptide binding agent in addition to a first biomarker polypeptide binding agent. The second binding agent may be any of the entities discussed above with respect to the first binding agent, such as an antibody. It is contemplated that a second antibody may bind to the same or different epitopes as the first antibody. It is also contemplated that the second antibody may bind the first antibody or another epitope than the one recognized by the first antibody.

As discussed earlier, binding agents may be labeled or unlabeled. Any biomarker polypeptide binding agent used in methods of the invention may be recognized using at least one detection agent. A detection agent may be an antibody that binds to a biomarker polypeptide binding agent, such as an antibody. The detection agent antibody, in some embodiments, binds to the Fc-region of a binding agent antibody. In further embodiments, the detection agent is biotinylated, which is incubated, with a second detection agent comprising streptavidin and a label. It is contemplated that the label may be radioactive, fluorescent, chemiluminescent, an enzyme, or a ligand. In some cases, the label is an enzyme, such as horseradish peroxidase.

The present invention also covers methods involving using an ELISA assay to identify a soluble biomarker polypeptide. In some embodiments, the ELISA assay is a sandwich assay. In a sandwich assay, more than one antibody will be employed. Typically ELISA methods can be used, wherein the wells of a microtiter plate are coated with a set of antibodies which recognize the protein of interest. A sample containing or suspected of containing the protein of interest is then added to the coated wells. After a period of incubation sufficient to allow the formation of antibody-antigen complexes, the plate(s) can be washed to remove unbound moieties and a detectably labeled secondary binding molecule added. The secondary binding molecule is allowed to react with any captured sample marker protein, the plate washed and the presence of the secondary binding molecule detected using methods well-known in the art.

Other methods of the invention further include assaying a sample for a cell-bound polypeptide in addition to a soluble polypeptide. The second assay may be performed on the same sample as the identification of a soluble biomarker polypeptide or it may be performed on a different sample. It is contemplated that a sample may or may not include cells.

Also herein described is a method of selecting, for a subject having a tumor, in particular a metastatic melanoma, prostate or colon cancer, a treatment comprising an immunotherapeutic molecule acting on the subject's T cells efficient against the tumor of the subject, which method comprises a step a) of determining the sCD25, IL-2, IL-15, and/or sCD122 basal expression level(s), and optionally the LDH basal expression level, in a biological sample of the subject having a tumor, before any administration to the subject of an immunotherapeutic molecule for treating the subject's tumor, a step a') of determining, in a biological sample of the subject having a tumor, the sCD25, IL-2, IL-15, and/or sCD122 response expression level(s), and optionally the LDH basal expression level, after the administration to said subject of at least one therapeutic dose of the immunotherapeutic molecule for treating the tumor, and a step b) of comparing said response expression level to said basal expression level and to a reference expression level in a control population, i) a response expression level identical to the basal expression level or below the reference expression level being the indication that an immunotherapeutic molecule acting on the subject's T cells will not be efficient alone in the subject, and a step c) of selecting an appropriate treatment of the subject's tumor, preferably combining said immunotherapeutic molecule with an additional compound preferably selected from interleukin-2 (IL-2), IL-2 superkine, interleukin-15 (IL-15), sushi IL-15, radioimmunoconjugate of anti-CD25 and immunotoxin; and on the contrary ii) a response expression level above both the basal expression level and the reference expression level being the indication that the immunotherapeutic molecule acting on the subject's T cells is as such (alone) efficient against the tumor of the subject.

Whatever the nature of the cancer, the accurate selection of the patients capable of responding to a particular immunotherapy is a solution for them to receive the most appropriate therapy as soon as possible and typically at the beginning of the treatment protocol.

Preferably, the additional compound is administered intravenously, preferably orally.

In a particular embodiment, the additional compound (for example recombinant IL-15 or sushi IL-15) is administered intravenously to a human being suffering from a metastatic melanoma once a day for 12 consecutive days at doses for example of 0.25, 0.5, 1, 2, 3, 7, 10, 15 or 20 micrograms per kilogram. Such protocols and doses will be easily adapted by the skilled person depending on the subject and the tumor said subject is suffering from.

In a particular embodiment in relation to the previously described method, when the immunotherapeutic treatment, typically the anti-CTLA-4, anti-PD-1, anti-PDL-1, anti-PDL-2, anti-Tim3, anti-Lag3, anti-VISTA, anti-BTLA, or anti-OX40 antibody or a combination thereof, is not efficient alone in the subject, the appropriate treatment is a combination of said immunotherapeutic treatment with a compound selected from interleukin-2 (IL-2), IL-2 superkine, interleukin-15 (IL-15), sushi IL-15, radioimmunoconjugate of anti-CD25, immunotoxin, and any combination thereof.

Also herein described is a method of identifying an inappropriate treatment of a tumor for a subject having a tumor, comprising applying the previously described method and, for a subject for whom the immunotherapeutic molecule is identified as being efficient as such against the subject's tumor, applying an additional step d) of determining, in a biological sample of said subject, the sCD25, IL-2, IL-15, and/or sCD122 response expression level(s), and optionally the LDH expression level, after the administration to said subject of the second therapeutic dose of the immunotherapeutic molecule for treating the tumor, an increase of the sCD25, IL-2, IL-15, and/or sCD122 response expression level(s), and optionally of the LDH expression level, when compared to the sCD25, IL-2, IL-15, and/or sCD122 response expression level(s), and optionally to the LDH expression level, determined after the administration to said subject of the first therapeutic dose of the immunotherapeutic molecule for treating the tumor, being the indication that the immunotherapeutic molecule is toxic for the subject and is an inappropriate treatment of a tumor for the subject.

In the methods herein described of assessing the sensitivity of a subject having a tumor to an immunotherapeutic molecule as well as in the methods herein described of selecting an appropriate treatment of cancer, any classical method known by the skilled person of determining the presence or measuring the expression level of a compound of interest, such as, typically, ELISA and radioimmunoassay, can be used.

In some embodiments the invention relates to a method for monitoring the immunotherapeutic treatment of a subject suffering from a cancer, comprising i) determining the level(s) of a sCD25, IL-2, IL-15, sLAG3 and/or sCD122 polypeptide(s), and optionally the LDH expression level, in a sample obtained from the subject before any immunotherapeutic treatment, ii) determining the level of the sCD25, IL-2, IL-15, and/or sCD122 polypeptide(s), and optionally the level of LDH polypeptide, in a sample obtained from the subject after said subject has been administered a first dose of the immunotherapeutic treatment, iii) comparing the level determined at step i) with the level determined at step ii), and iv) concluding that the immunotherapeutic treatment is effective when the level(s) determined at step ii) is/are increased when compared to the level(s) determined at step i) or concluding that the immunotherapeutic treatment is not effective when the level(s) determined at step ii) is/are identical to or below the level(s) determined at step i).

Methods of screening for candidate therapeutic agents for preventing or treating cancer are also included as part of the invention.

A method herein described is a method for screening or identifying a compound suitable for improving the treatment of a cancer in a subject having a tumor, said method comprising determining the ability of a test compound to modify the expression of sCD25, IL-2, IL-15, and/or sCD122, and optionally of LDH, or compensate for an abnormal expression thereof.

In some embodiments, the present invention relates to a method of screening for candidate therapeutic agents for a cancer, comprising i) providing a plurality of candidate compounds, ii) bringing the candidate compounds into contact for example with T cells containing mononuclear cells or with purified T cells harvested from blood or lymph nodes or tumor beds, with or without stimulation with anti-CD3/CD28 or PMA/ionomycine and/or ICOS ligands to monitor the release, in the supernatants, of candidate molecules of interest (such as sCD25, IL-2, IL-15, sLAG3, and sCD122, and optionally LDH), iii) determining the levels of the sCD25, IL-2, IL-15, and sCD122 polypeptide(s), and optionally LDH polypeptide, expressed/released by activated T cells or preparations enriched with such T cells, iv) comparing the level(s) determined at step iii) with the level(s) determined in the absence of the candidate compounds, and v) positively selecting the candidate compounds when the level(s) determined at step iii) is increased when compared to the level(s) determined in the absence of the candidate compounds.

Typically the candidate compound may be selected from the group consisting of peptides, peptidomimetics, small organic molecules, antibodies, aptamers or nucleic acids. For example, the candidate compound according to the invention may be selected from a library of compounds previously synthesised, or a library of compounds for which the structure is determined in a database, or from a library of compounds that have been synthesised de novo.

In a particular embodiment, the candidate compounds may be selected from small organic molecules. As used herein, the term "small organic molecule" refers to a molecule of a size comparable to those organic molecules generally used in pharmaceuticals. The term excludes biological macromolecules (e.g., proteins, nucleic acids, etc.); preferred small organic molecules range in size up to 2000 Da, and most preferably up to about 1000 Da.

The present invention also includes kits for assessing or monitoring the sensitivity of a subject having a tumor to an immunotherapeutic molecule acting on a subject's T cells, preferably selected from an anti-CTLA-4, anti-PD-1, anti-PDL-1, anti-PDL-2, anti-Tim3, anti-Lag3, anti-VISTA, anti-BTLA and anti-OX40 antibody (either mono- or polyclonal). Such a kit comprises detection means, possibly in suitable container means, selected from the group consisting of at least one antibody specific to sCD25, IL-2, sLAG3, IL-15, and/or sCD122 polypeptide binding agent (typically an antibody specific to the soluble biomarker); a molecule allowing the antibody's detection; preferably at least one molecule allowing LDH detection (as routinely performed by the skilled person of the art); and, optionally, a leaflet providing the respective reference expression level(s) of sCD25 IL-2, sLAG3, IL-15, sCD122 and/or LDH in a biological sample from a control or reference population.

In further embodiments, the binding agent is labeled or a detection agent is included in the kit. It is contemplated that the kit may include a biomarker polypeptide binding agent attached to a non-reacting solid support, such as a tissue culture dish or a plate with multiple wells. It is further contemplated that such a kit includes a detectable agent in certain embodiments of the invention. In some embodiments the invention concerns kits for carrying out a method of the invention comprising, in suitable container means: (a) an agent that specifically recognizes all or part of an sCD25, IL-2, sLAG3, IL-15, sCD122 and/or LDH polypeptide(s); and (b) a positive control that can be used to determine whether the agent is capable of specifically recognizing all or part of an sCD25, IL-2, sLAG3, IL-15, sCD122 and/or LDH polypeptide(s). The kit may also include other reagents that allow visualization or other detection of the sCD25, IL-2, sLAG3, IL-15, sCD122 and/or LDH polypeptide(s), such as reagents for colorimetric or enzymatic assays.

Also included herein is the use of a kit as herein described for assessing or monitoring the sensitivity of a subject having a tumor to an immunotherapeutic molecule acting on a subject's T cells, preferably selected from an anti-CTLA-4, anti-PD-1, anti-PDL-1, anti-PDL-2, anti-Tim3, anti-Lag3, anti-OX40, anti-BTLA4, and/or anti-VISTA antibody (either mono- or polyclonal).

The invention will be further illustrated by the following figures and examples. However, these figures and examples should not be interpreted in any way as limiting the scope of the present invention.

MCA 205 OVA (A) or MC38-OVA$^{dim}$ (B) tumor cell lines have been inoculated subcutaneously in C57/B16 mice. When tumor sizes reach 30-40 mm$^2$, mice receive 100 µg of anti-CTLA4 every 3 days during 12 days, as indicated. Tumor sizes are monitored every 2-3 days until mice are sacrificed. p<0.05; *p<0.01 T test. (n=5 mice/group).

Figure 2:
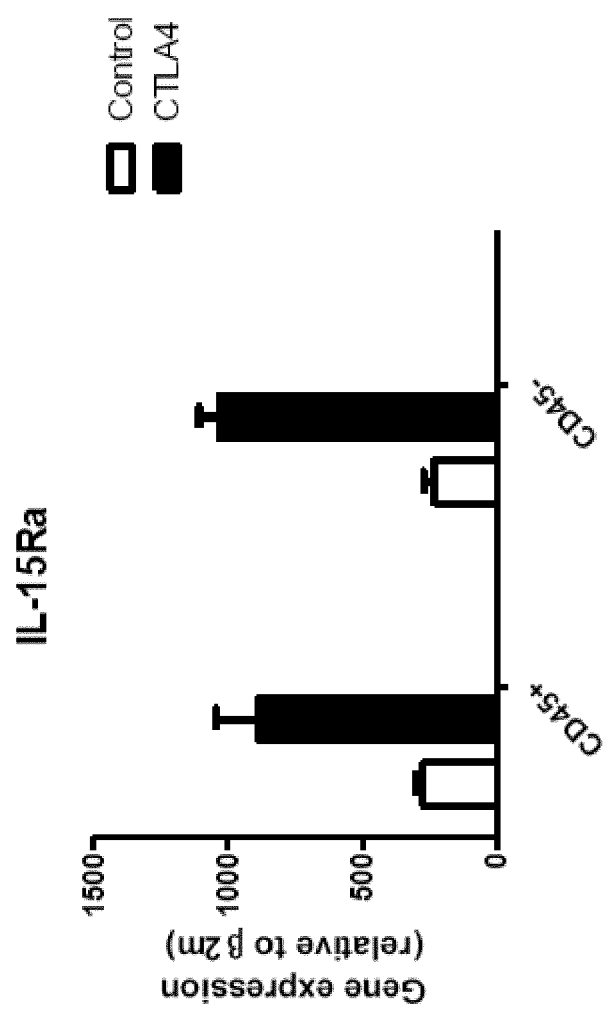

FIG. 2: IL-15Rα is up regulated post-anti-CTLA4 by both tumoral and intratumoral leukocytic fractions.

Figure 1:
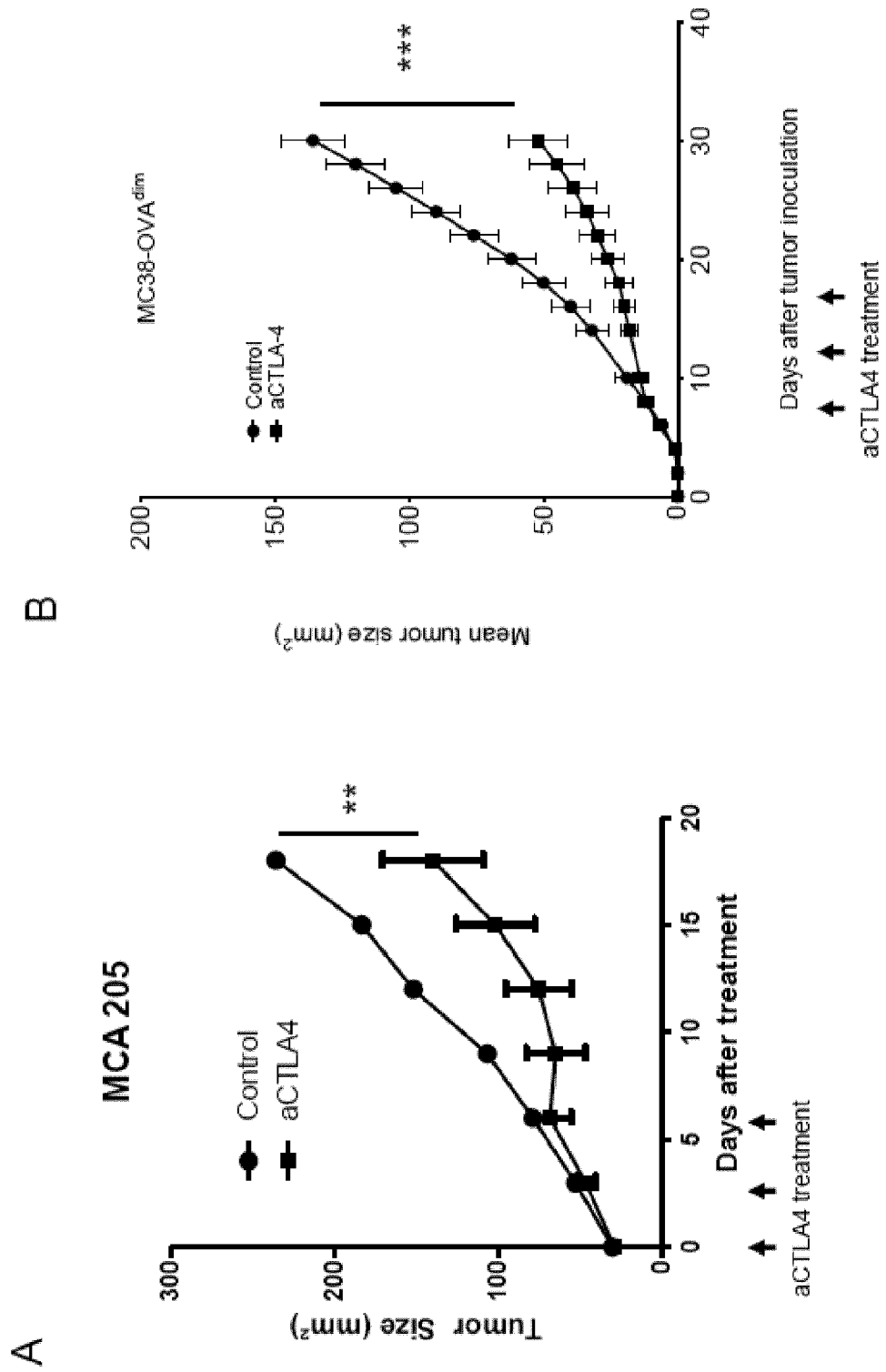
FIG. 1: Murine anti-CTLA4 induces the control of tumor growth.

MCA 205 OVA tumors have been harvested from mice that have received 3 anti-CTLA4 injections (as described in FIG. 1), 2 days after the last injection. Tumors have been digested and a CD45 magnetic cell separation has been performed to separate CD45− (Tumor) and CD45+(Leukocytes). The expression of IL-15Rα has been assessed by qRT-PCR. Results are expressed relative to β2 microgloubuline expression. (n=5 mice/group).

Figure 3:
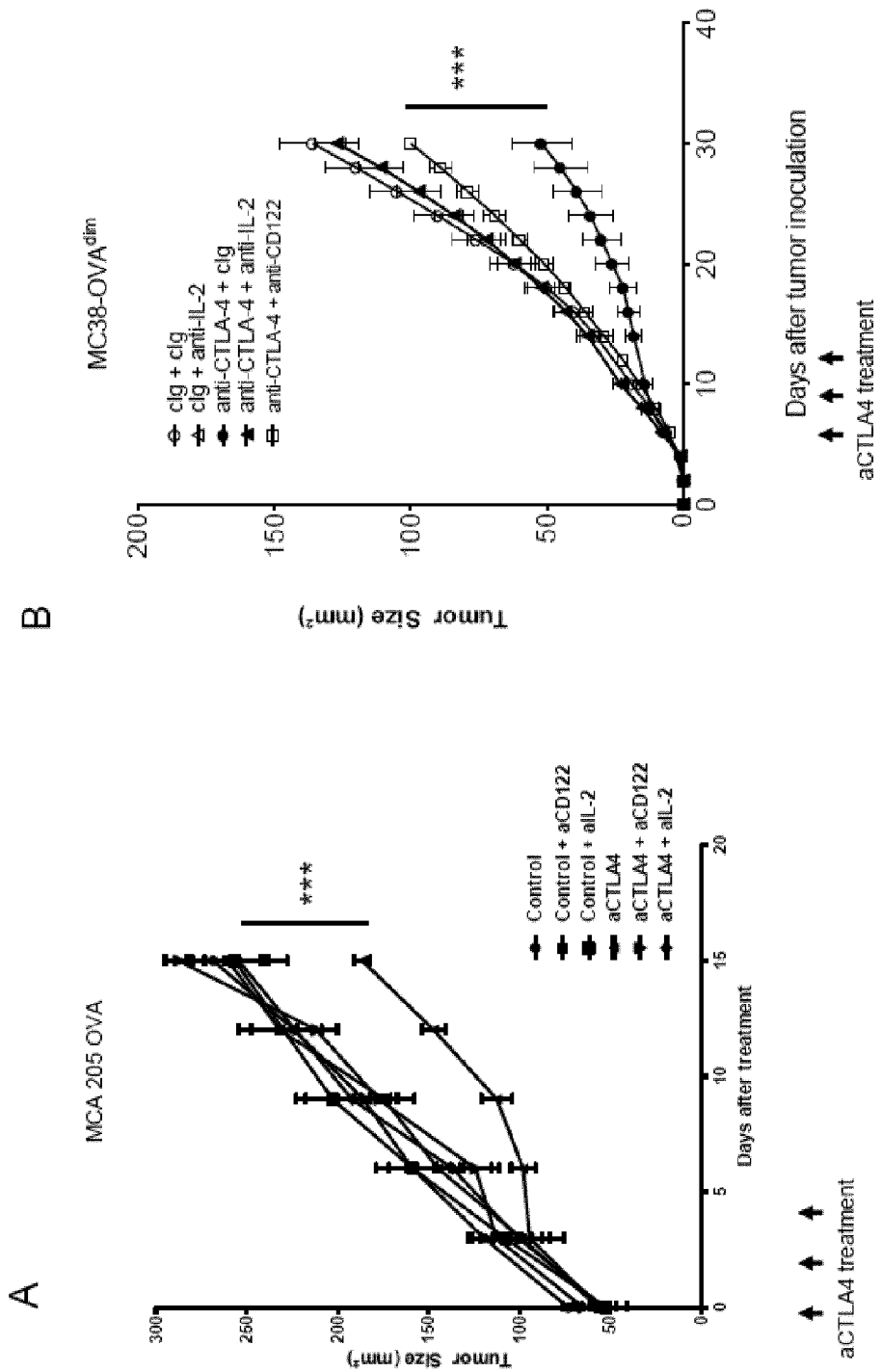

FIG. 3: IL-2/CD122 axis is critical for anti-CTLA4 efficacy.

MCA 205 OVA (A) or MC38-OVA$^{dim}$ (B) tumor cell lines have been inoculated subcutaneously in C57/B16 mice. When tumor sizes reach 30-40 mm$^2$, mice receive 100 µg of anti-CTLA4 every 3 days for 12 days, as indicated. Anti-CD122 (100 µg/mouse, i.p. injected) or anti-IL-2 (50 µg/mouse, i.t. injected) neutralizing antibodies have been injected every 3 days throughout the experiment to block either the receptor or the cytokine. Tumor sizes are monitored every 2-3 days until mice sacrifice. ***p<0.01 T test. (n=5 mice/group).

Figure 4:
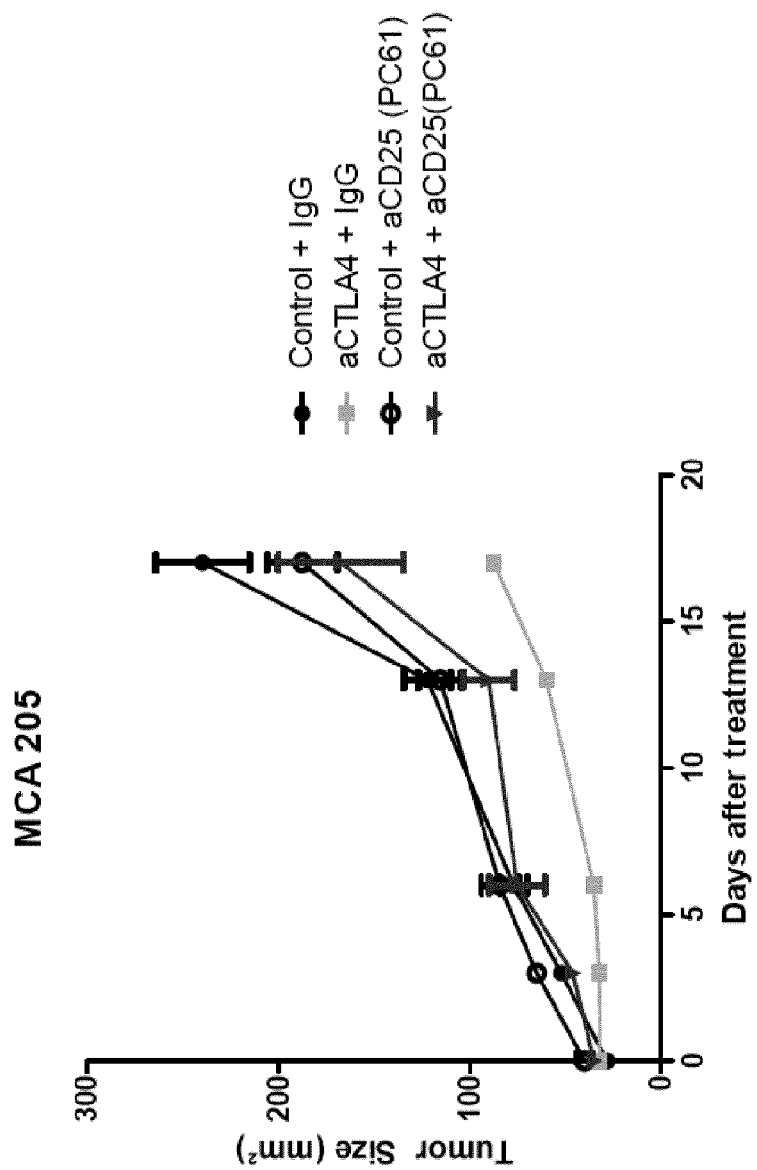

FIG. 4: IL-2Rα (CD25) axis is critical for anti-CTLA4 efficacy.

MCA 205 OVA tumors have been inoculated subcutaneously in C57/B16 mice. When tumor sizes reach 30-40 mm², mice receive 100 μg of anti-CTLA4 every 3 days for 12 days, as indicated. Anti-CD25 neutralizing Ab or IgG control Ab (500 μg/mouse, i.p. injected) have been injected 1 day before tumor inoculation and 1 day before anti-CTLA4 treatment. Tumor sizes are monitored every 2-3 days until mice sacrifice. ***p<0.01 T test. (n=5 mice/group).

Figure 5:
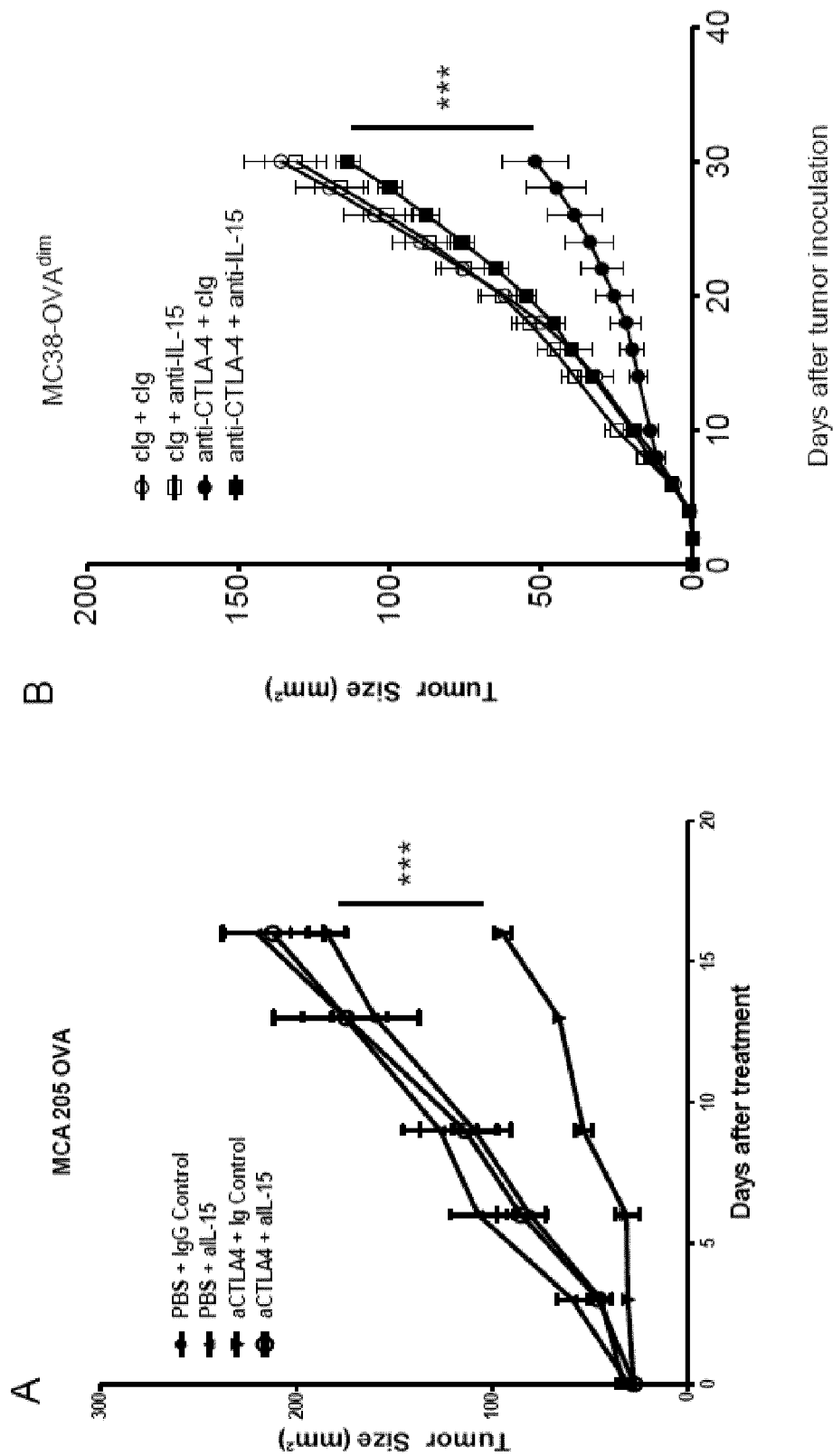

FIG. 5: IL-15 (recognized by CD122) is also critical for anti-CTLA4 efficacy.

MCA 205 OVA (A) or MC38-OVA$^{dim}$ (B) tumor cell lines have been inoculated subcutaneously in C57/B16 mice. When tumor sizes reach 30-40 mm², mice receive 100 μg of anti-CTLA4 Ab every 3 days for 12 days, as indicated. Anti-IL-15 (50 μg/mouse, i.t. injected) neutralizing Ab have been injected every 3 days throughout the experiment to neutralize the cytokine. Tumor sizes are monitored every 2-3 days until mice sacrifice. ***p<0.01 T test. (n=5 mice/group).

Figure 6:
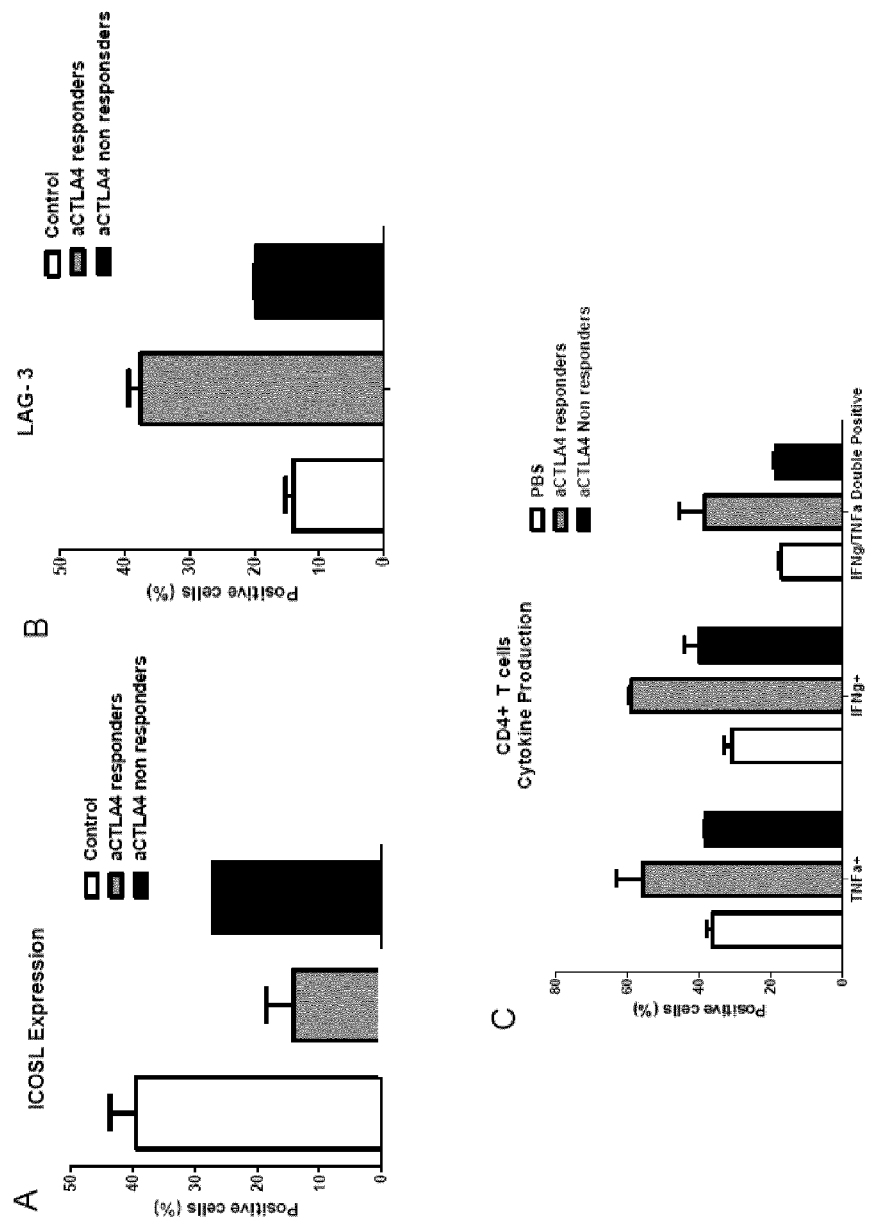

FIG. 6: Mice exhibiting a significant anticancer response to anti-CTLA4 Ab display a loss of ICOSL$^+$CD4+ T cells and an accumulation of LAG-3+CD4+ T cells among Tumor Infiltrating Leukocytes.

MCA 205 OVA tumors have been harvested from mice that have received 3 anti-CTLA4 Ab injections, 2 days after the last injection. Flow cytometry analyses have been performed. ICOSL (A) and LAG-3 (B) expression by CD4$^+$ T cells are presented. Panel C shows the cytokine production (IFNγ and TNFα) by CD4+ T cells following PMA/ionomycin stimulation, followed by intracellular staining for flow cytometry analysis. (n=5 PBS group; n=3 anti-CTLA4 Ab responders; n=2 anti-CTLA4 Ab non responders).

Figure 7:
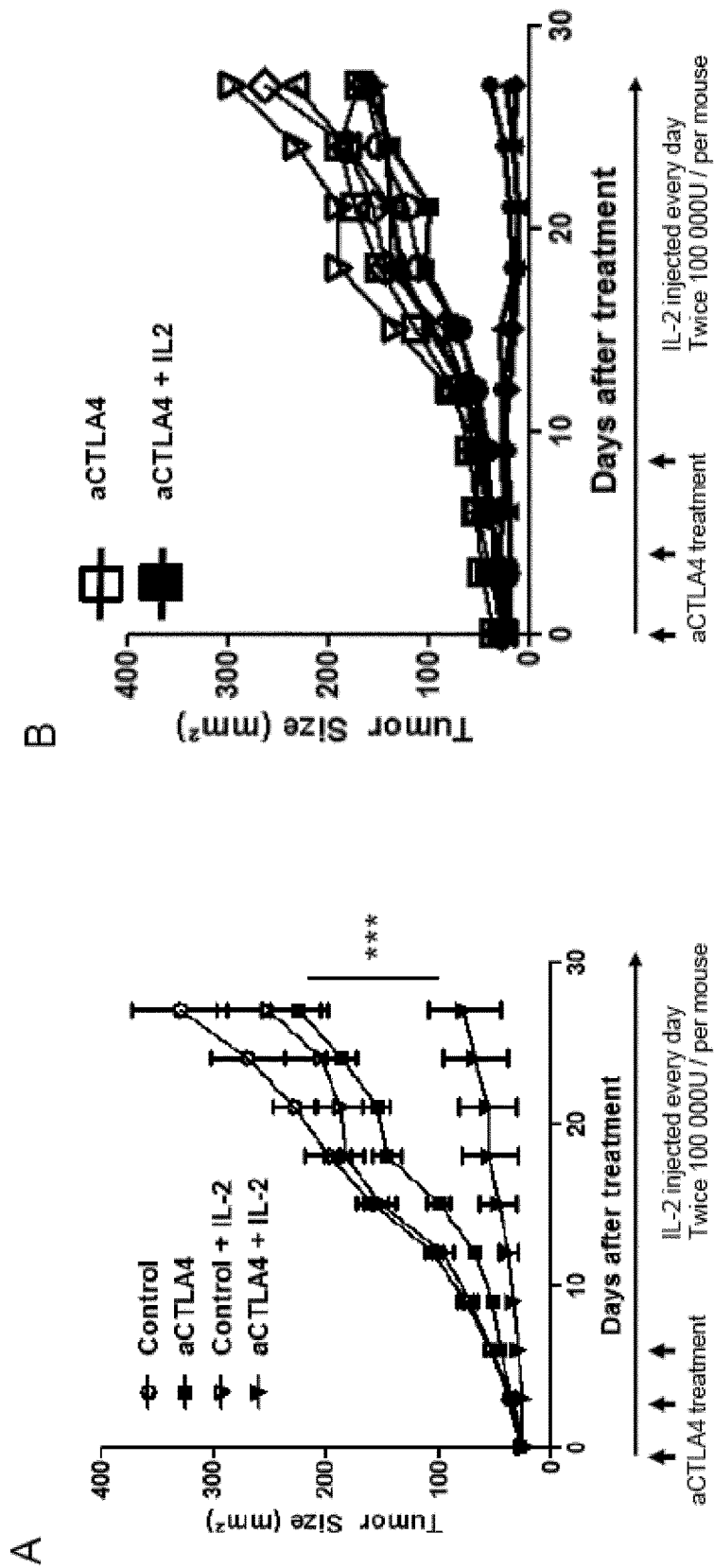

FIG. 7: Synergistic effect between anti-CTLA4 Ab and rIL-2.

MCA 205 OVA tumors have been inoculated subcutaneously in C57/B16 mice. When tumor sizes reach 30-40 mm², mice receive 100 μg of anti-CTLA4 Ab every 3 days for 12 days, as indicated. 100,000 U of rIL-2 have been injected twice a day every day throughout the experiment, as indicated. (A) Means of tumor growth over time. (B) Tumor growth curves of each mouse treated by anti-CTLA4Ab alone or in combination with IL-2. (n=5 mice/group).

Figure 8:
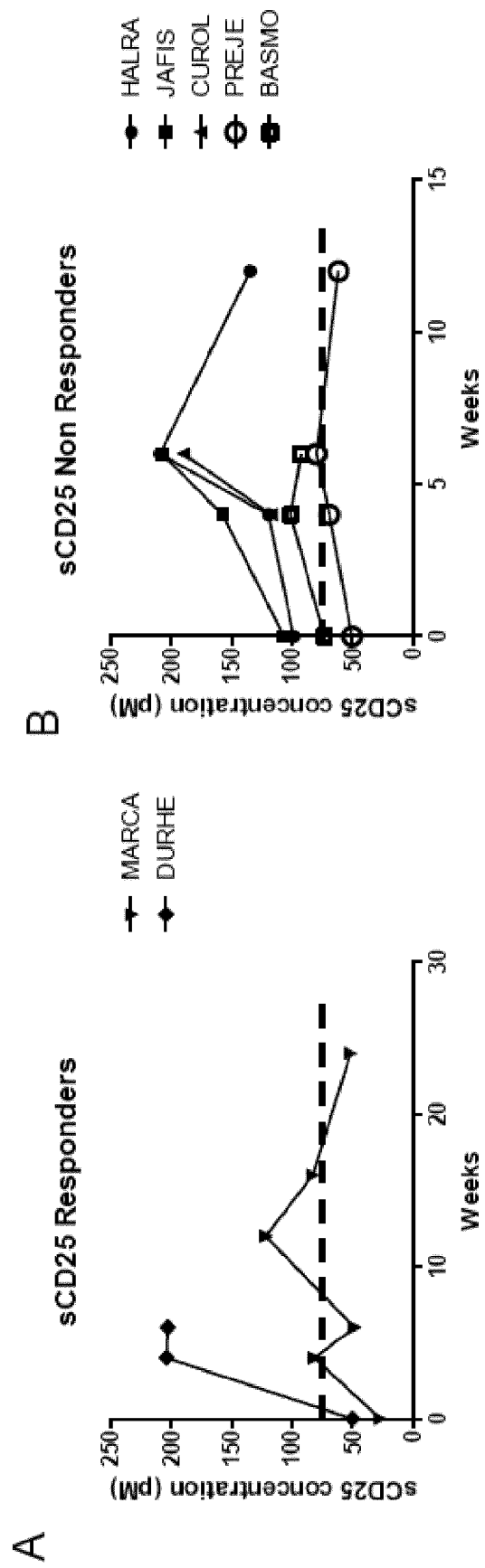

FIG. 8: Follow-up of sCD25 overtime in metastatic melanoma patients treated by 10 mg/kg of Ipilimumab, associated with radiotherapy.

(A) Responding patients; (B) non-responding patients. Dashed line: Positivity threshold 80 pMol/L.

Figure 9:
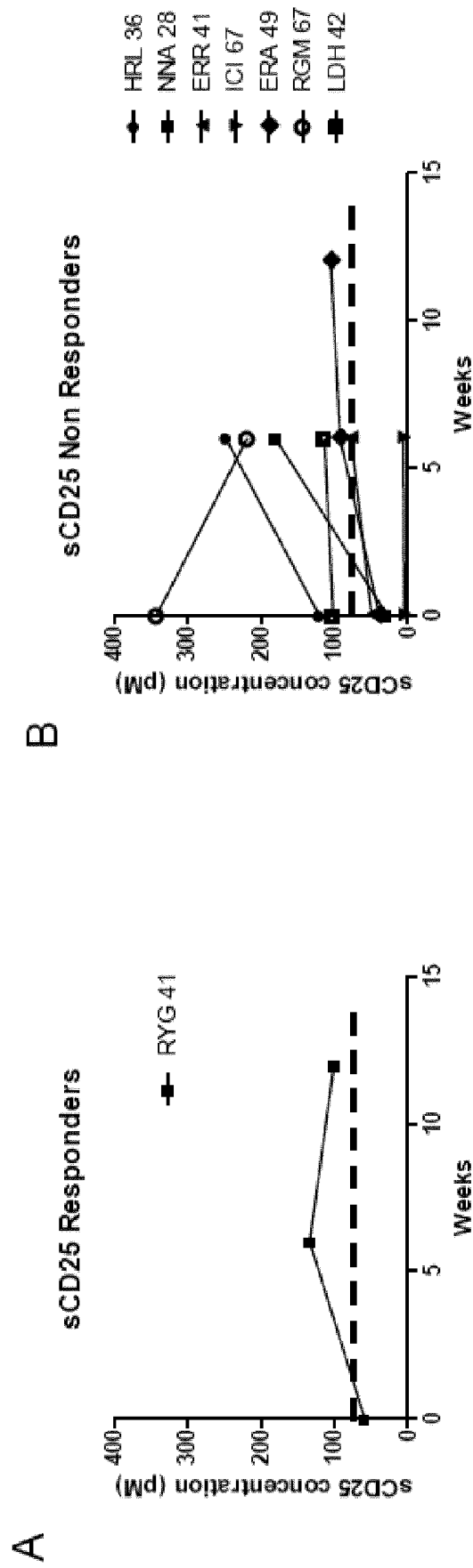

FIG. 9: Follow-up of sCD25 overtime in metastatic melanoma patients treated by 3 mg/kg of Ipilimumab.

(A) Responding patients; (B) non-responding patients. Dashed line: Positivity threshold 80 pMol/L.

Figure 10:
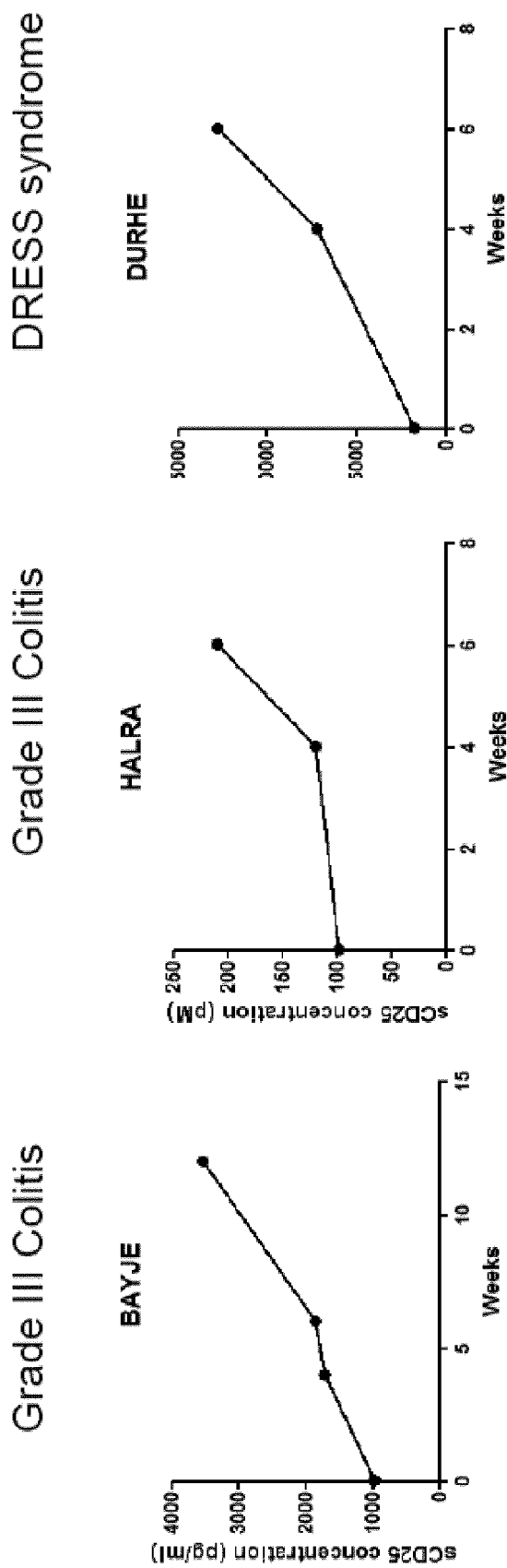
Figure 11:
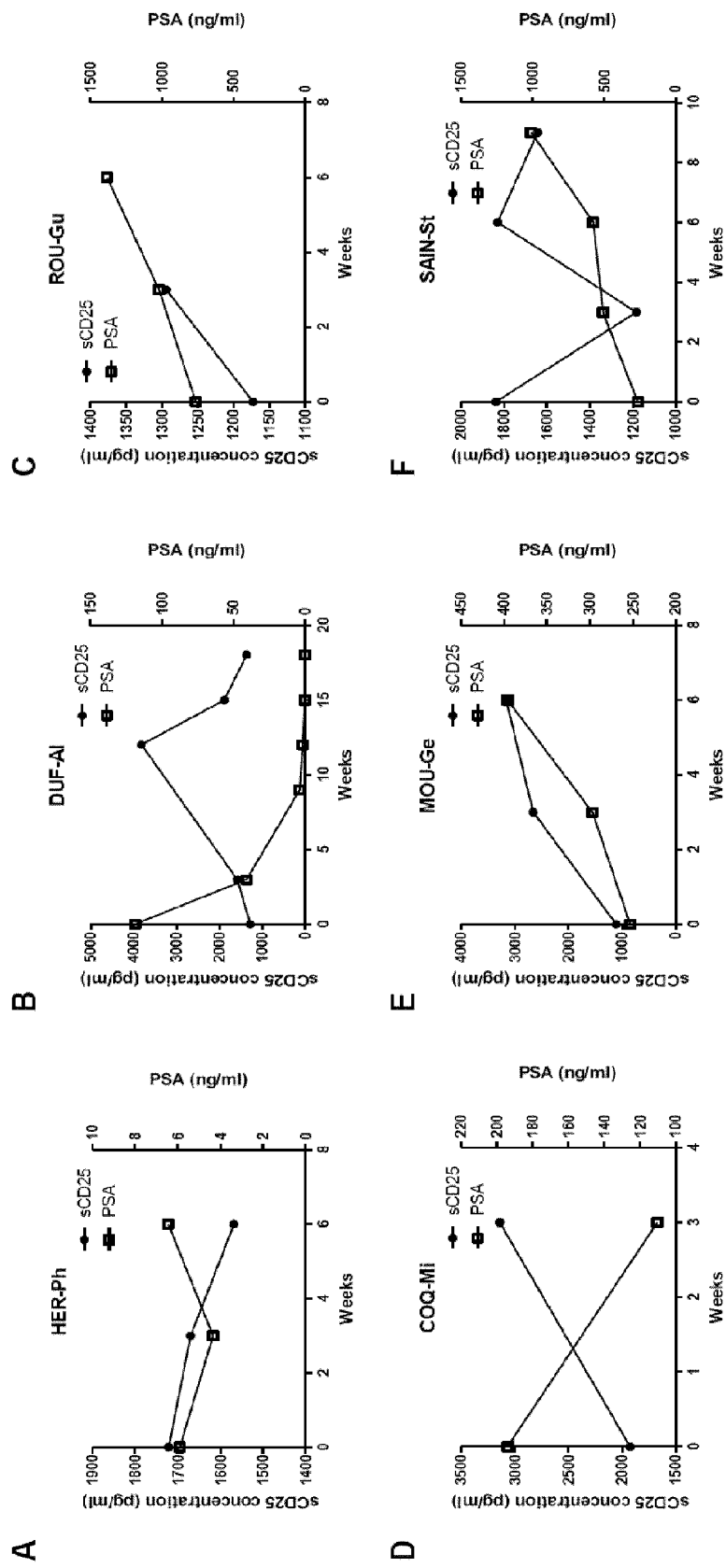
Figure 11:
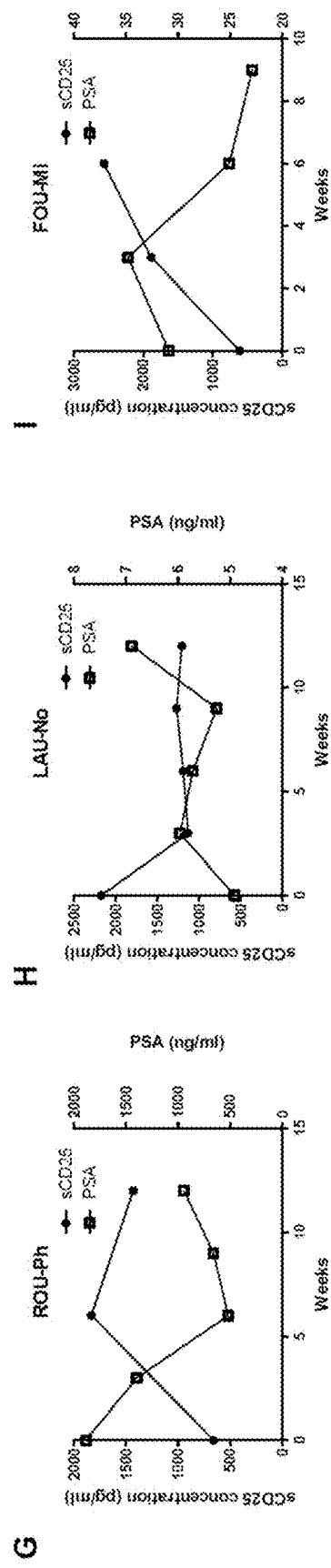

FIG. 10: Continuous increase of sCD25 in metastatic melanoma patients that have developed severe Ipilimumab-related toxicity.

Serum level of sCD25 post-C2 is superior to post-C1 which is superior to baseline (before treatment). All these patients are from cohort #1. HALRA and BAYJE experienced grade III colitis and DURHE experienced a DRESS syndrome.

FIGS. 11A-11I: sCD25 serum level seems to inversely correlate with PSA serum level in hormono-resistant prostate cancer patients treated by 10 mg/kg Ipilimumab.

Each graph shows 1 patient. pPanel B shows the responding patient.

Figure 12:
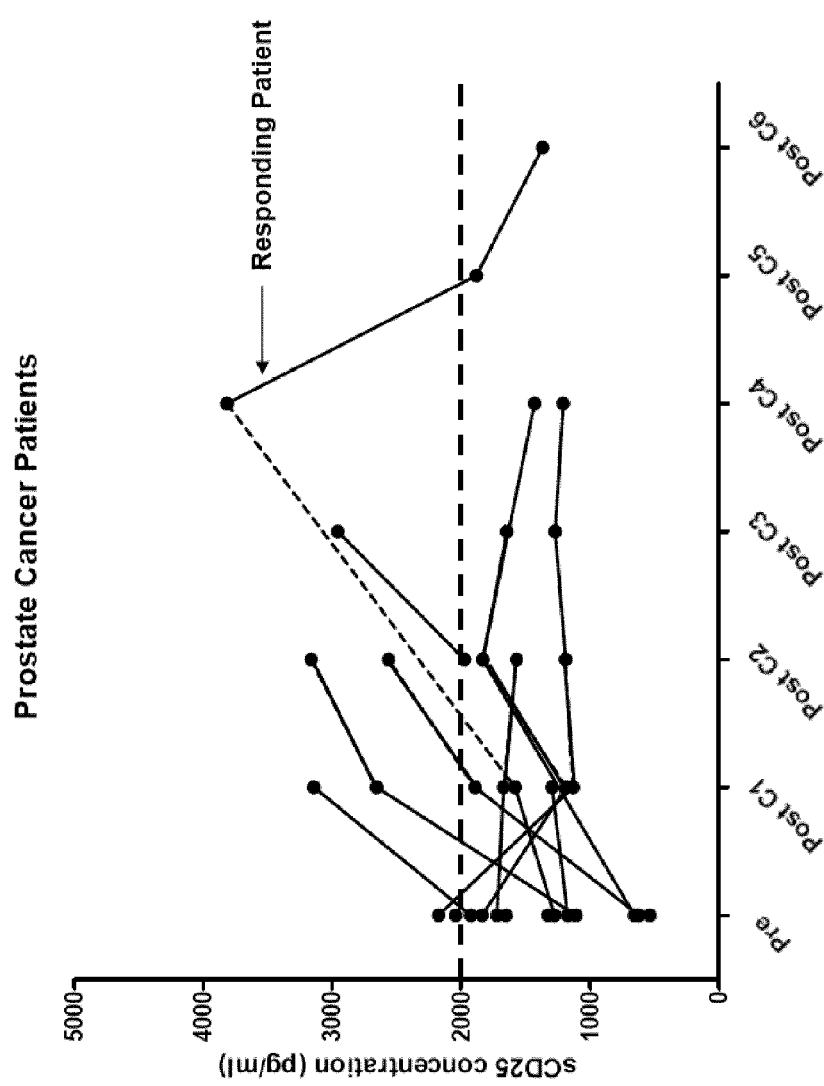

FIG. 12: Follow-up of sCD25 serum level overtime in hormonoresistant prostate cancer patients treated by 10 mg/kg of Ipilimumab.

The responding patient is indicated. Dashed line: Positivity threshold 2000 pg/ml.

Figure 13:
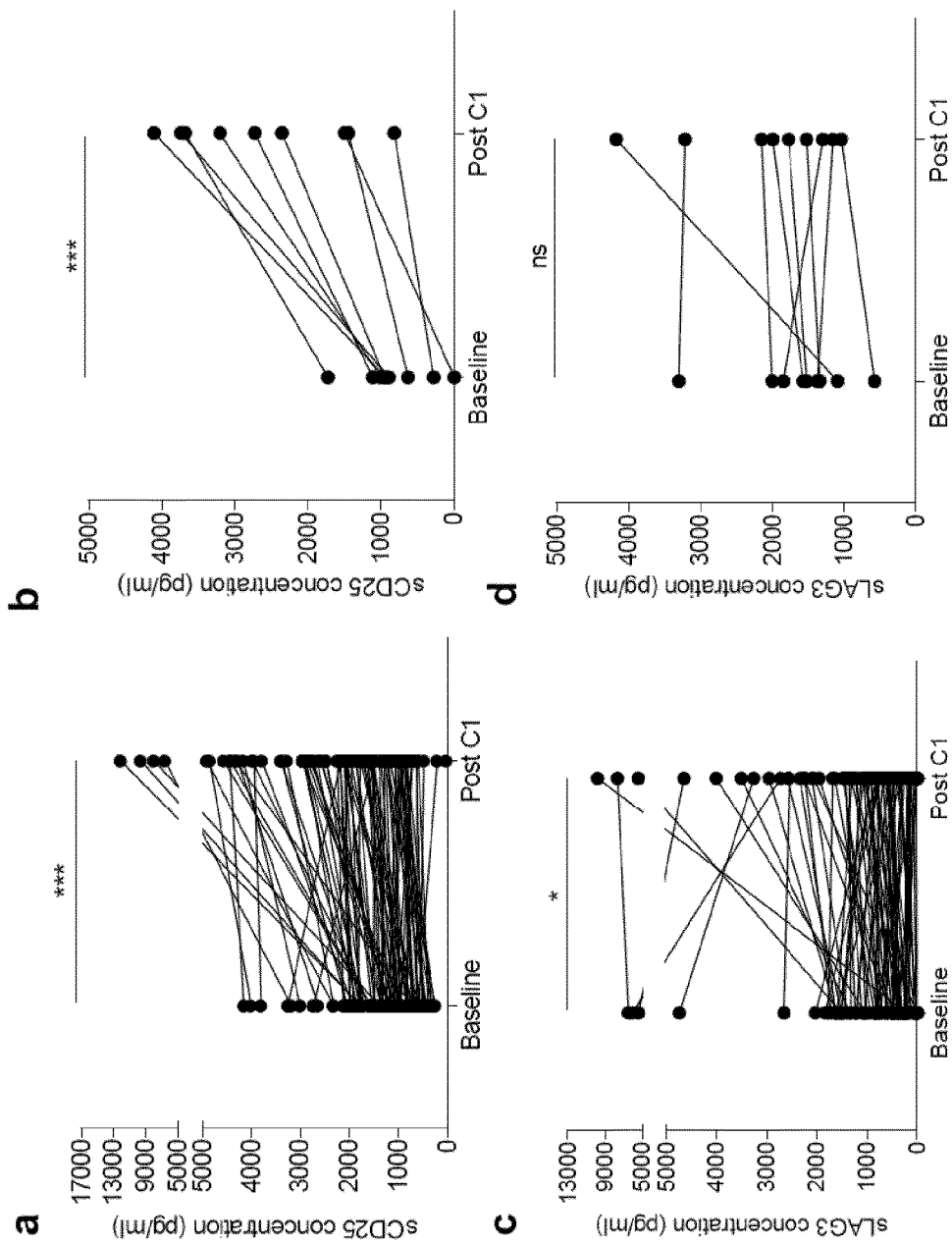
Figure 13:
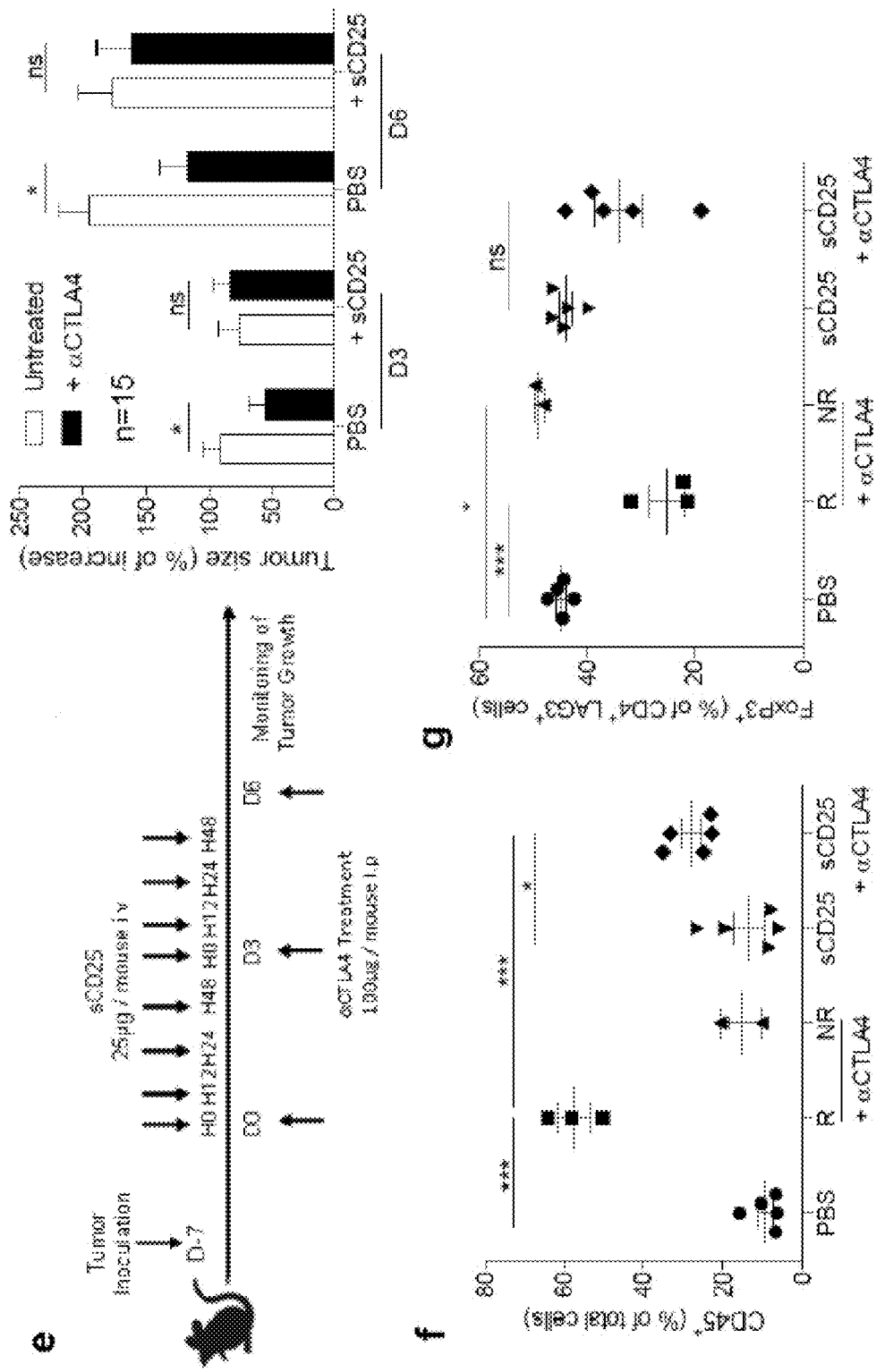

FIG. 13: High serum levels of soluble CD25 compromise the efficacy of anti-CTLA4 blockade in mice.

a-d. Serum levels of sCD25 and sLAG3 in patients. Eight independent cohorts of 262 MM were analyzed and compared with one cohort of 9 patients treated with rIL-2 for an autoimmune disorder (Saadoun et al.). Graphs depict the ELISA-determined concentrations of sCD25 (a-b) or sLAG3 (c-d) in the serum prior to and 3 weeks after ipilimumab (a-c) or rIL-2 (b-d), respectively. Each dot represents one patient. Paired Student's t-test:* p<0.05, ***p<0.001, ns: not significant. e. Inhibitory effects of high concentrations of sCD25 on the efficacy of ipilimumab in mice. 2 mg of sCD25 was administered systemically i.v. prior to and following the two first injections of anti-CTLA4 Ab in MCA205-OVA tumor bearers (left panel). Tumor sizes (one dot/tumor) were monitored for the first 8 days of sCD25 administration at three time points (day 0, at start, day+3 and day+6) and compared with untreated tumors (empty dots). Groups comprised 5 mice and three experiments were performed and concatenated. Mean tumor sizes of 15 mice/group are shown at day 3 and day 6 post-first ipilimumab injection (right panel) while each tumor is depicted at various kinetics in FIG. 14a. f-g. The effects of sCD25 on the composition of TILs were examined in each group: treated with ipilimumab, responding (R) or not (NR), and coadministered with sCD25. Flow cytometry analyses of CD45$^+$ cells among live cells (f) and CD4$^+$Lag3$^+$Foxp3$^+$ TILs (g), each dot representing one tumor specimen. Paired Student's t-test or ANOVA:* p<0.05, p<0.01, *p<0.001, ns: not significant.

Figure 14:
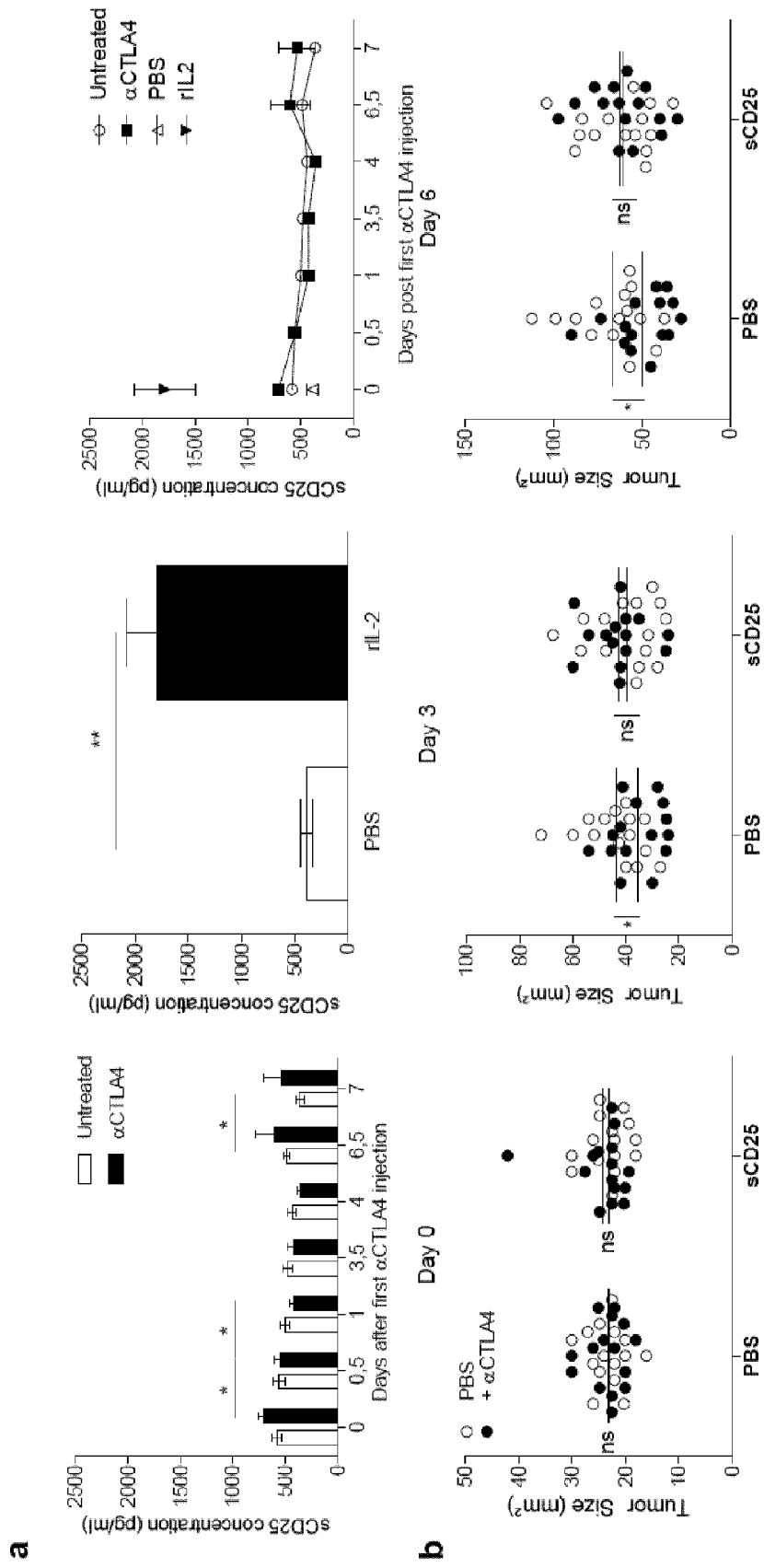
Figure 14:
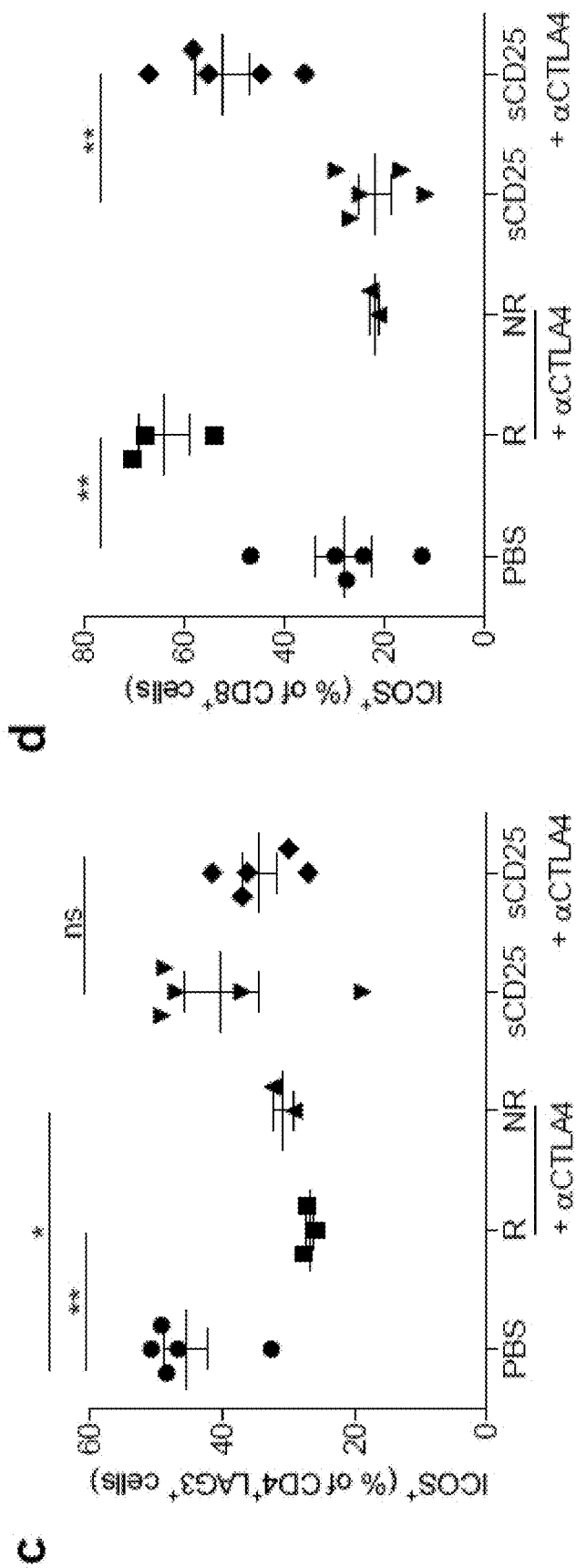

FIG. 14: Inhibitory effects of high concentrations of sCD25 on the efficacy of ipilimumab in mice.

a. Lack of measurable sCD25 in mice receiving anti-mCTLA-4 Ab. Kinetic study of sCD25 concentrations in the serum of tumor-bearing mice treated with anti-mCTLA-4 or mice that did not receive tumors, treated with high dosing of rIL-2 (100,000 IU twice a day for 4 days) using commercial ELISA. b. 2 mg of sCD25 was administered systemically i.v. prior to and following the two first injections of anti-CTLA-4 Ab in MCA205-OVA tumor bearers (FIG. 6e, left). Tumor sizes (one dot/tumor) were monitored for the first 8 days of sCD25 administration at three time points (day 0, at start, day+3 and day+6) to ipilimumab-treated (black dots) or PBS-treated (empty dots) tumors and compared with mice which did not receive sCD25. Groups comprised 5 mice and three experiments were performed and concatenated. Each tumor is depicted at various kinetics with one dot. c-d. The effects of sCD25 on the composition of TILs were examined in each group: treated with ipilimumab, responding (R) or not (NR), and coadministered with sCD25. Flow cytometry analyses of ICOS expression on CD4$^+$Lag3$^+$ TILs (b) and CD8$^+$TILs (c), each dot representing one tumor specimen. Paired Student's t-test or ANOVA:* p<0.05, p<0.01, *p<0.001, ns: not significant.

Figure 15:
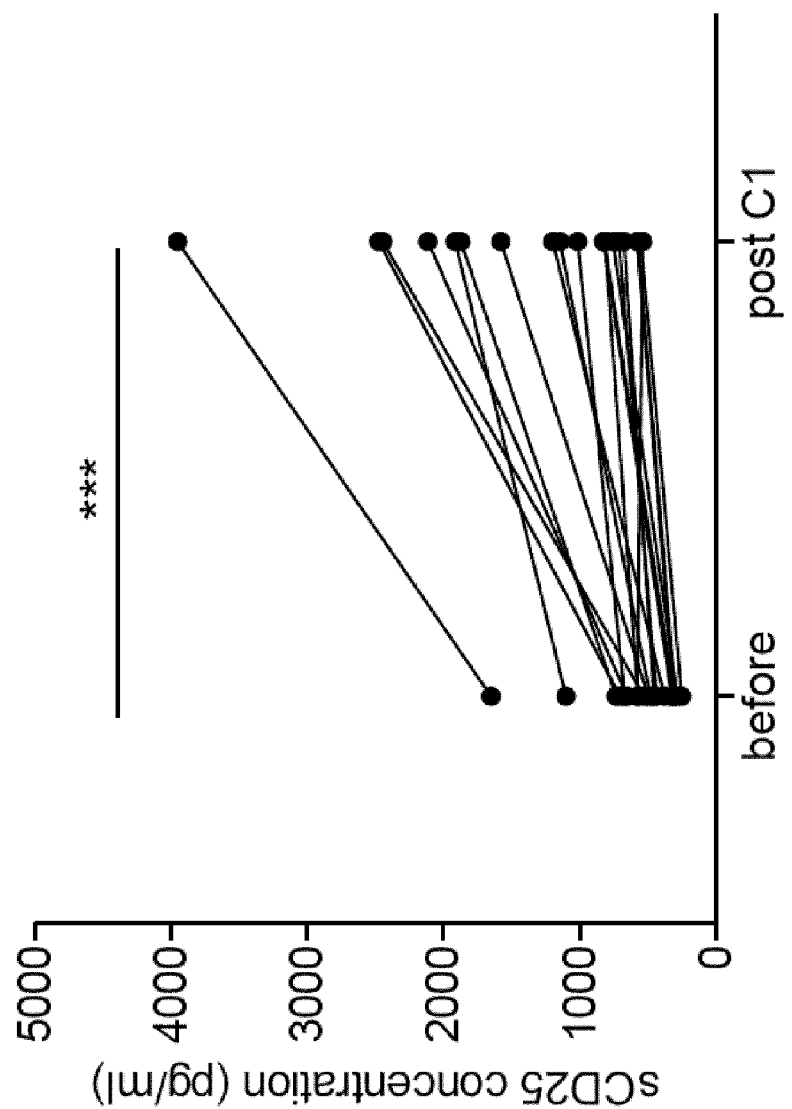
Figure 16:
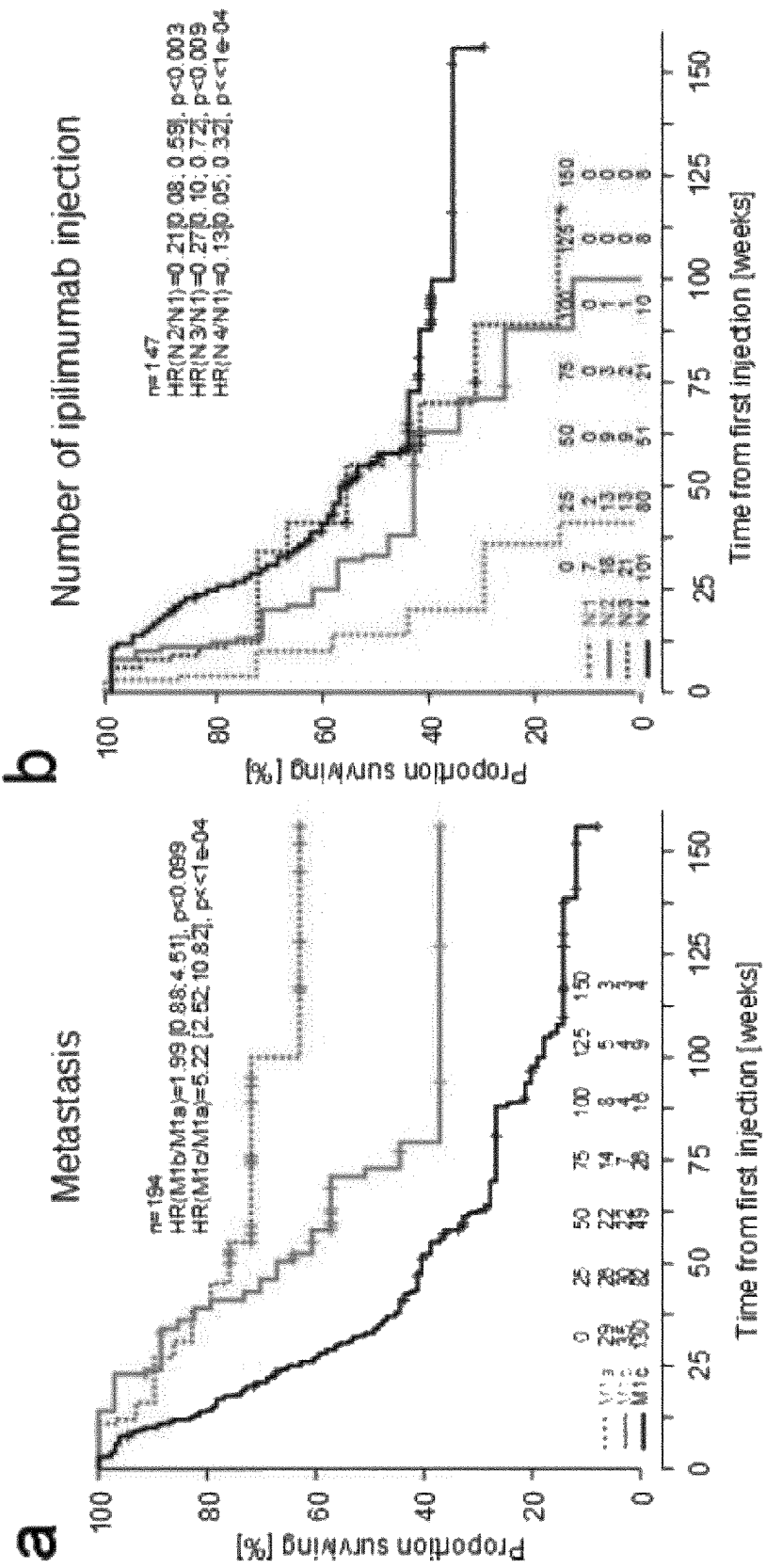
Figure 16:
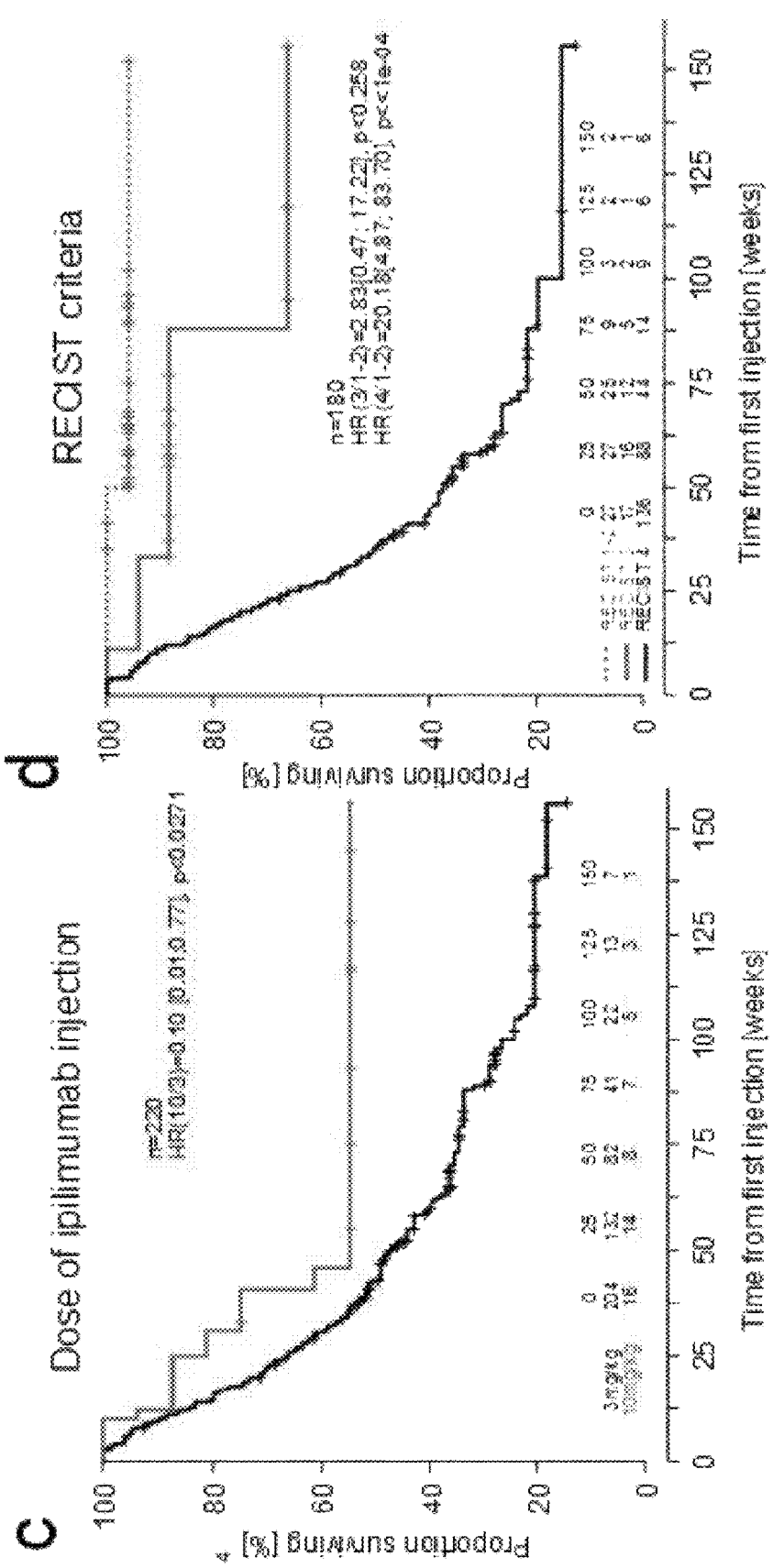
Figure 16:
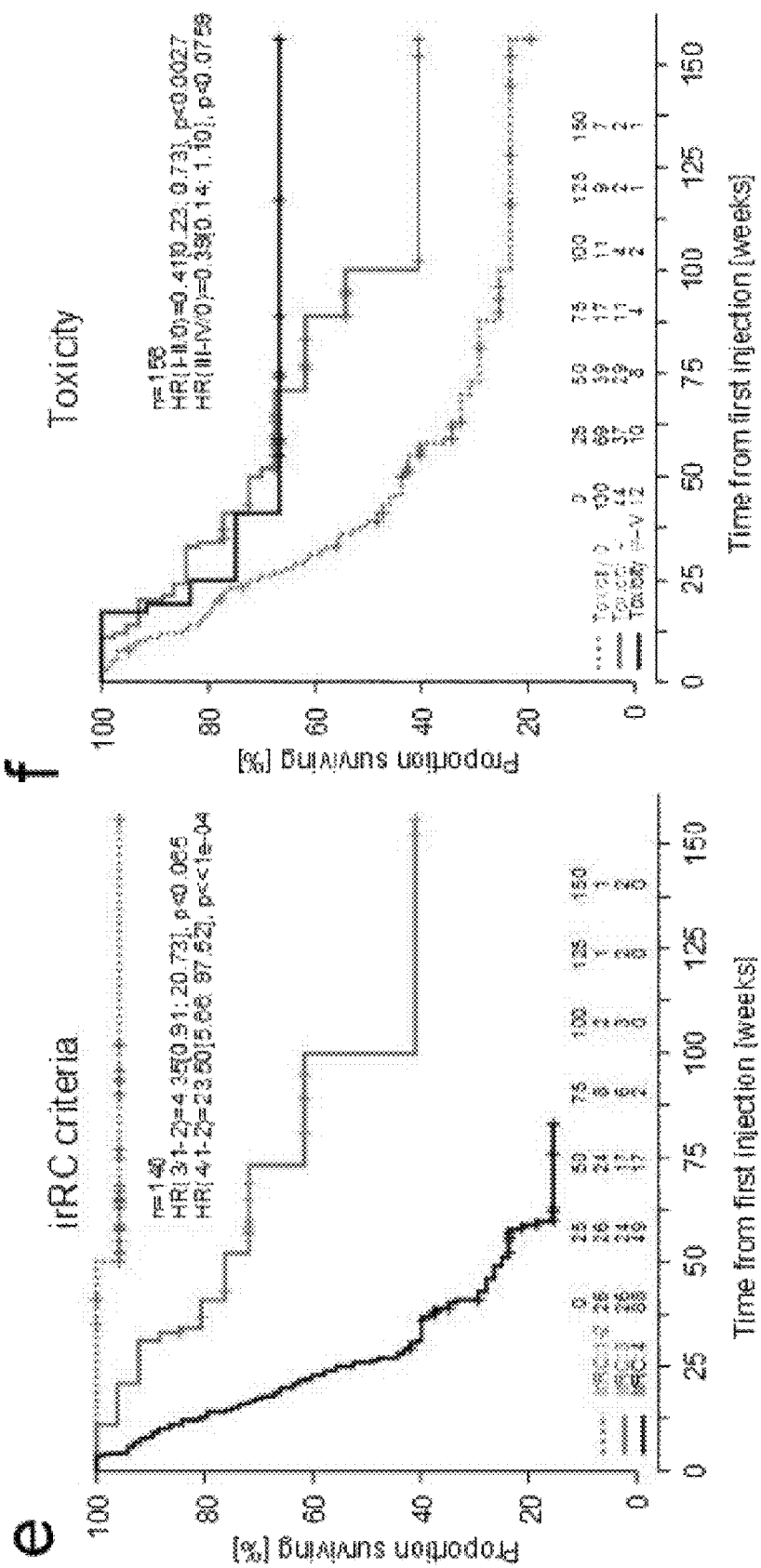

FIG. 15: Tremelimumab induced a rise in the levels of serum sCD25.

A cohort of 20 MM patients described in Ribas et al. received 15 mg/kg of Tremelimumab. Serum levels of sCD25 have been evaluated in ELISA before and 3 weeks after the first injection (C1). Paired Student's t test:* p<0.05.

FIGS. 16a-f: Univariate analyses of multiple parameters of clinical significance for OS of MM patients.

According to the data presented in Table 2, each parameter (indicated above each graph) that was statistically associated with overall survival (except sCD25 and LDH featuring in FIG. 17) has been plotted over time (Log Rank survival curves). Statistical methods and results are either shown or explained in the Materials & Methods section.

Figure 17:
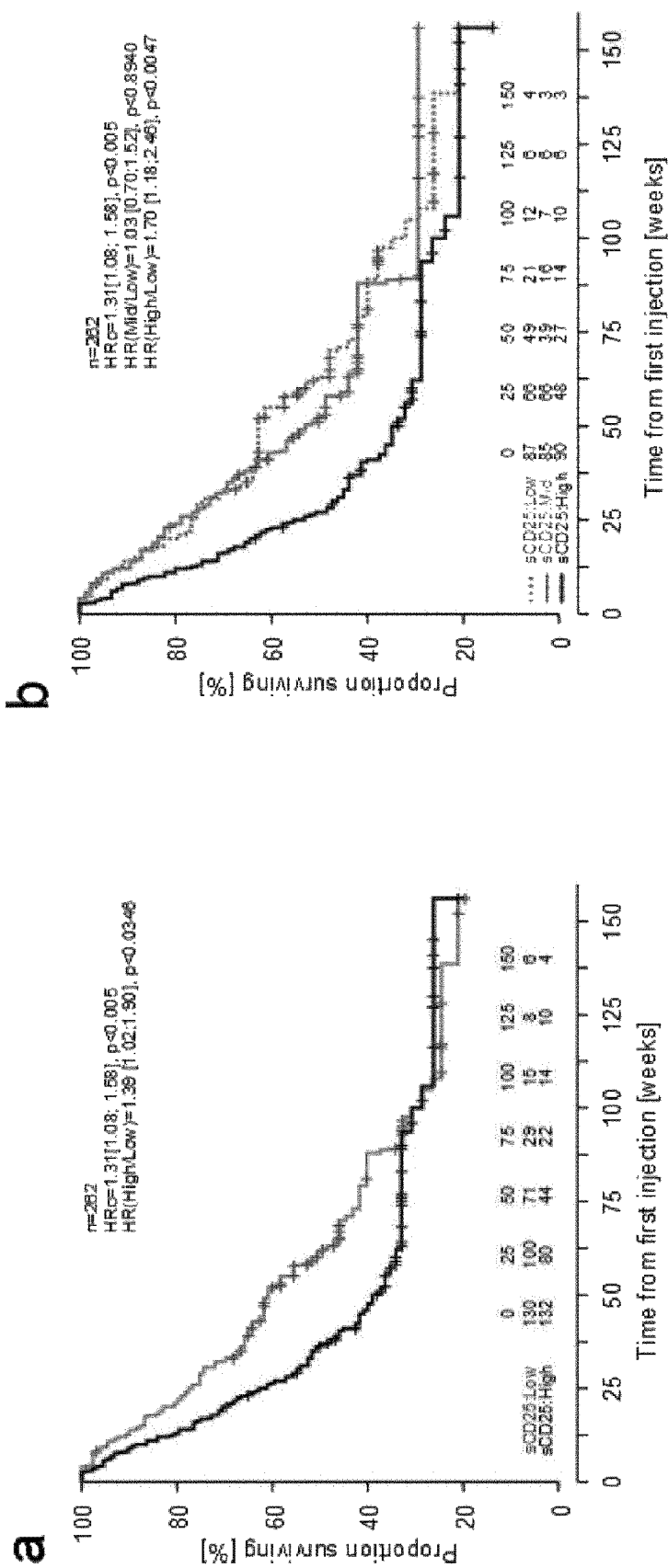
Figure 17:
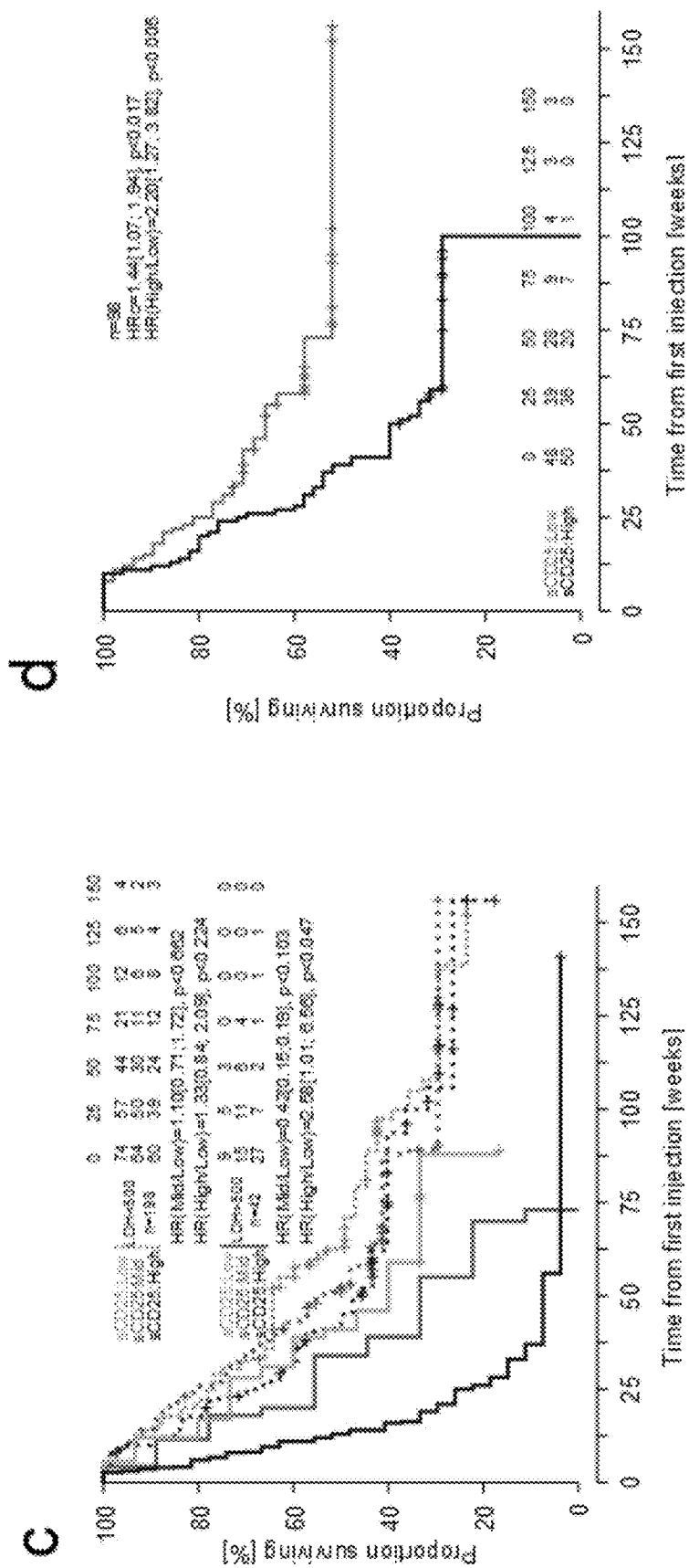

FIG. 17: Baseline sCD25 serum levels predict resistance to ipilimumab in humans.

a-b. Baseline serum levels of sCD25 and overall survival (OS). Kaplan-Meier curves in all of the 8 cohorts gathering 262 patients segregated into two groups according to the median LRT=4.69, p<0.030 (a) and the tercile LRT=9.17, p<0.010 (b) c. Baseline serum levels of sCD25 and LDH and OS. Kaplan-Meier curves of 249 MM patients segregated into 6 groups according to the median value of LDH (with 500 as the threshold, also herein identified as the cut-off value) and the tercile of sCD25 LRT=5.76 p=0.056 (c). d. Post-first ipilimumab serum levels of sCD25 and OS. Kaplan-Meier curves of 98 MM patients segregated into two groups according to the median value of sCD25 post C1 (3 weeks post-first ipilimumab injection). LRT=6.01, p<0.014.

Figure 18:
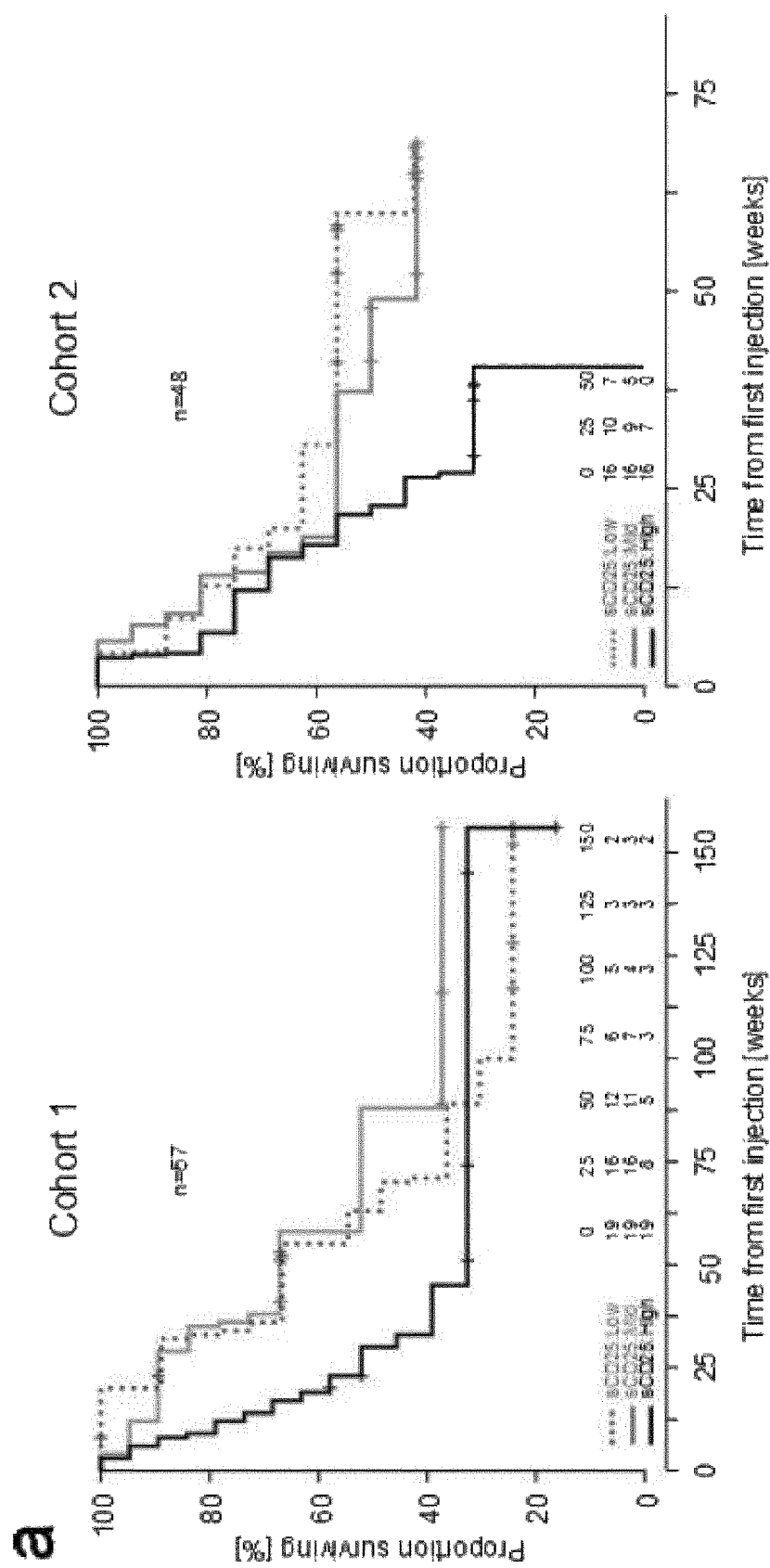
Figure 18:
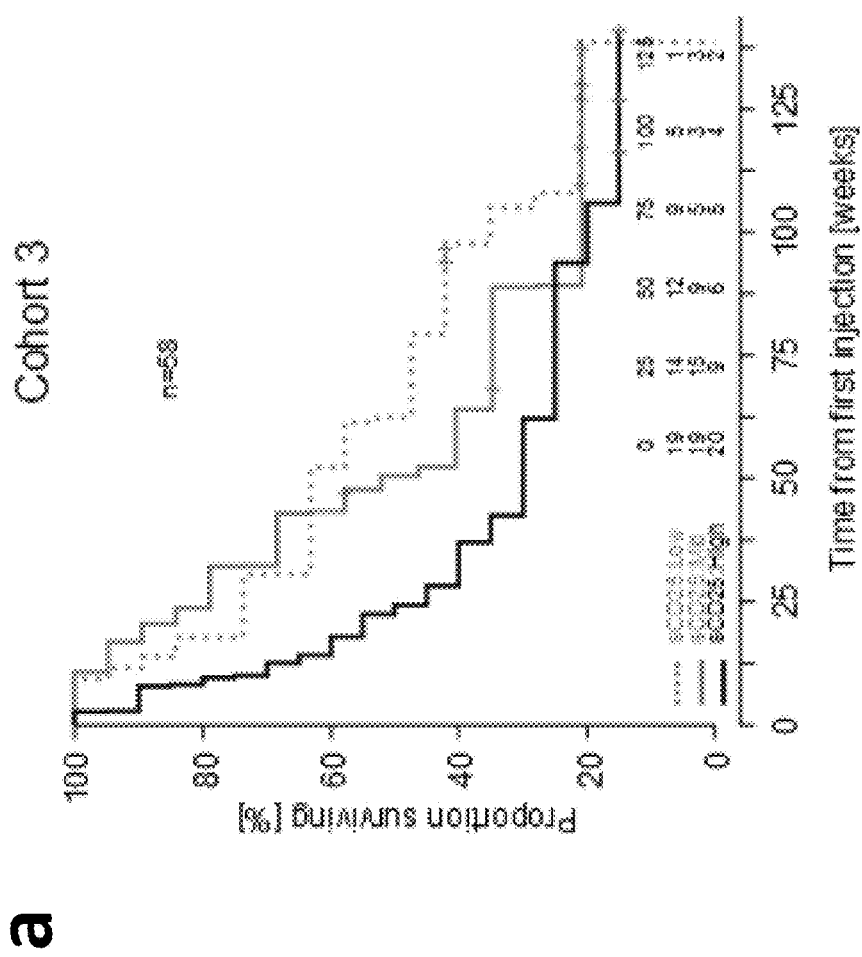
Figure 18:
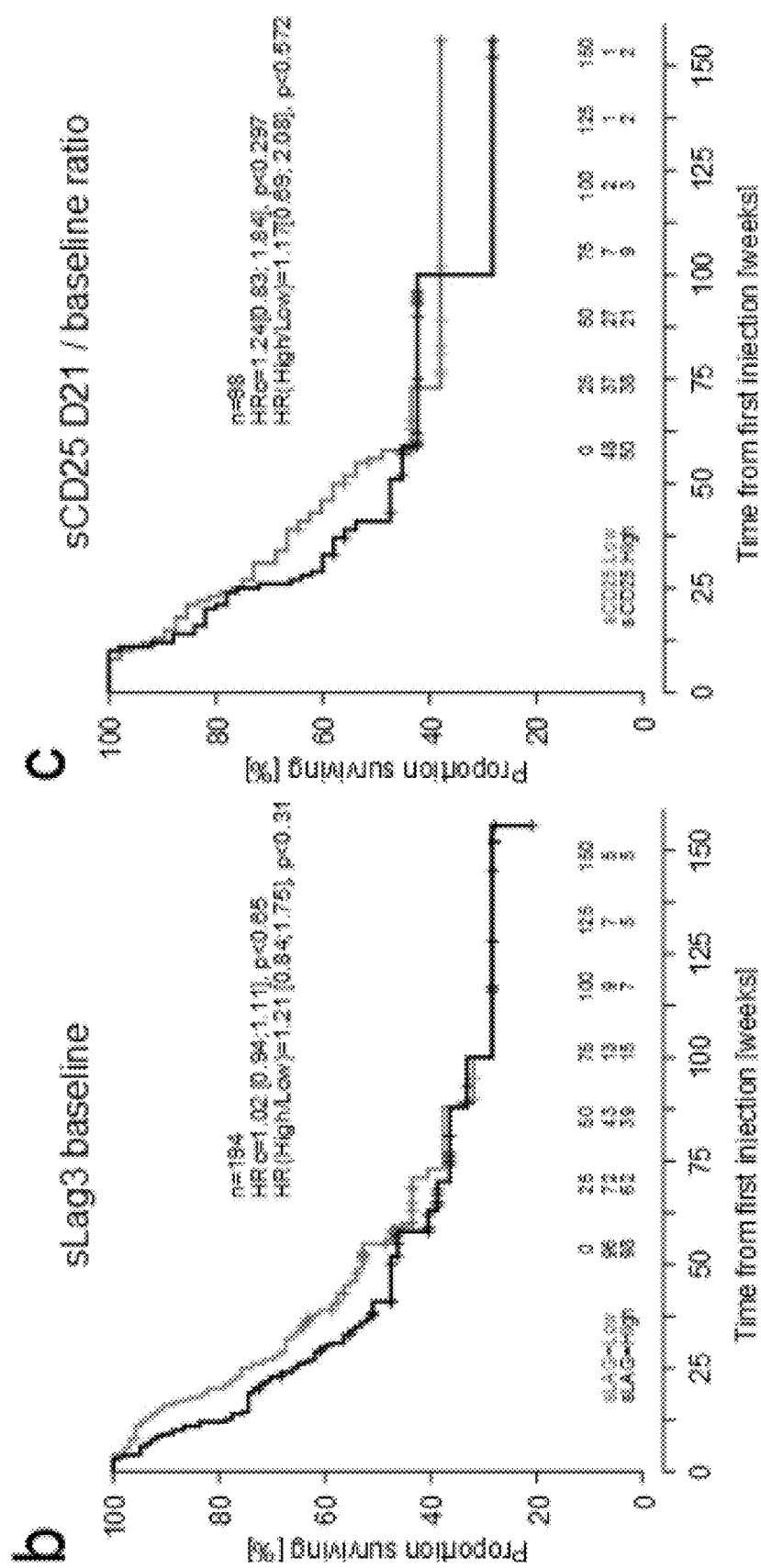

FIG. 18: sCD25 serum levels at T0 versus T21 and OS in MM patients.

a. Baseline serum levels of sCD25 and OS in three cohorts shown in details. Kaplan-Meier curves of 3 representative cohorts segregated into 3 groups according to the terciles. b. Baseline serum levels of sLAG3 and OS. Kaplan-Meier curves of 194 MM patients segregated into two groups according to the median LRT=1.28, p=0.257. c. Analysis of the ratio between post-C1 sCD25/baseline sCD25 and OS. A subgroup of 98 patients in the 262 aforementioned patients for whom samples at 1 injection were available was analyzed for the correlation between sCD25 post-C1/sCD25 baseline ratio and OS. LRT=1.04, p<0.007.

Figure 19:
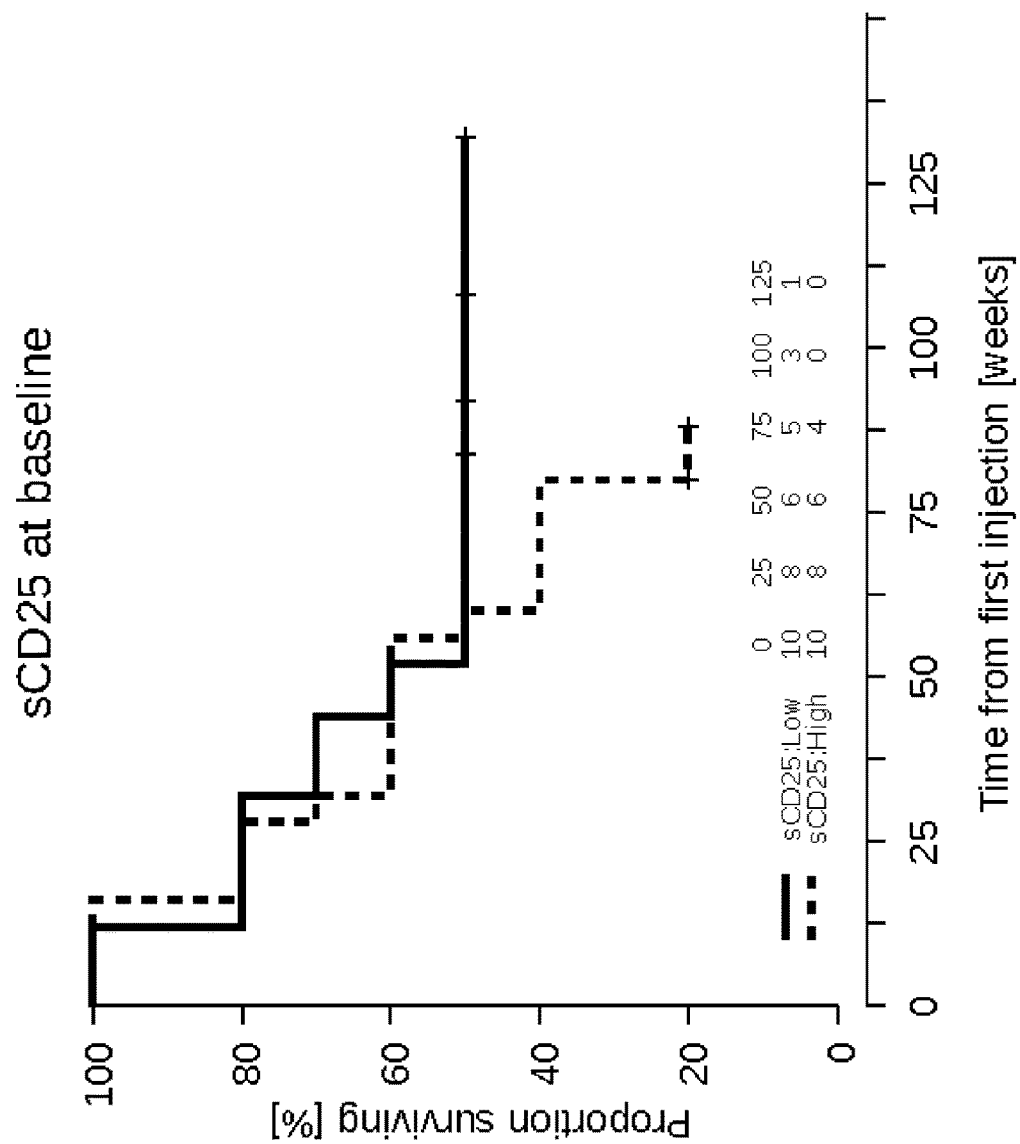

FIG. 19. Baseline sCD25 serum levels and overall survival in Tremelimumab-treated patients.

Baseline serum levels of sCD25 and overall survival (OS). Kaplan-Meier curves in a cohort of 20 patients segregated into two groups according to the median (490 pg/ml; HR: 1.58 [0.52; 4.82], p<0.3999).

Other characteristics and advantages of the invention are given in the following experimental section (with reference to FIGS. 1 to 19), which should be regarded as illustrative and not limiting the scope of the present application.

EXPERIMENTAL PART

Example 1—Prospective Study Using Ipilimumab

In a prospective study conducted by the inventors, patients were treated using Ipilimumab.

Inclusion criteria were: a diagnosis of unresectable stage III or IV melanoma, at least one previous line of chemotherapy, and survival 12 weeks after the first perfusion.

Four courses of Ipilimumab were administered at the dose of 3 mg/kg every 3 weeks. 3 patients were included. The median overall survival was 9.1 months (95% CI: 6.4-11.3) from the start of Ipilimumab. Immune-related adverse events were noted in 45 patients (62%), including 20 grade 3-4 events (27.4%). No drug-related death occurred. In univariate analysis, factors associated with improved overall survival were the number of Ipilimumab infusions (≥4), the lymphocyte count at the start of the second course (cut off level at 1000/mm$^3$), and an eosinophil count increase of more than 100>mm$^3$ between the first two infusions.

In small trials, it was shown that Ipilimumab results in the accumulation of ICOS-expressing CD4+ T cells (and to a lesser extent of CD8+ T cells) and TH17 cells. Inventors concluded that these criteria do not adequately predict the clinical benefit of Ipilimumab in Phase III trials.

Example 2—Soluble CD25 as a Predictive Marker of Response to Anti-CTLA4 Antibodies Material & Methods
Patient Cohorts
    Cohort 1: Ipilimumab associated with radiotherapy
    7 metastatic melanoma patients (4M and 3F, age: 45-80 years) received Ipilimumab (10 mg/kg, BMS) every 3 weeks for a total of 4 injections. Between the second and third injection, patients received fractioned radiotherapy (3×3Gy i.e., 9Gy in total over 1 week).
    Toxicities reported are mainly Grade II-III colitis.
    Cohort 2: Ipilimumab as monotherapy
    8 metastatic melanoma patients (age: 39-84 years) received Ipilimumab (3 mg/kg, BMS) every 3 weeks for a total of 4 injections
    Toxicities reported are diarrhea and hypophysitis.
    Cohort 3: Ipilimumab associated with radiotherapy
    9 hormonoresistant prostate cancer patients have been treated for bone metastases with the combination of local radiotherapy followed by 4 injections of Ipilimumab at 10 mg/kg, every 3 weeks.
    Cohort 4: 12 metastatic melanoma (MM) patients treated with 3 or 10 mg/kg
    Twelve MM patients have been treated either with 3 or 10 mg/kg of Ipilimumab 4 times, every 3 weeks.
Mice Tumor Models and Anti-CTLA4 Ab Treatment
    C57/B16 WT mice are provided by Harlan, France. For tumor inoculation: 1 million tumor cells (the fibrocarcoma cell line MCA 205 OVA or the colon carcinoma cell line MC38 OVA$^{dim}$) in 100 μl of PBS, in the right flank. When tumor size reaches 30-40 mm$^2$, mice are treated intraperitoneally (i.p.) with 100 μg of anti-CTLA4 Ab (Bio X Cell, Clone 9D9), 3 times every 3 days.
Neutralizing Antibodies
    Anti-IL-2 Ab (eBioscience, Clone: JES6-1A12) and anti-IL-15 Ab (eBioscience, Clone: AIO.3) or IgG control Ab (eBioscience, Rat IgG2a) have been injected intratumorally the same day as anti-CTLA4 treatment (20 μg in 50 μl of PBS). Anti-CD122 Ab (Bio X Cell, Clone: TM-beta1) have been injected every 3 days throughout the experiment starting from day 1 of anti-CTLA4 treatment to sacrifice.
    Anti-CD25 Ab (Bio X Cell, Clone: PC-61.5.3) or IgG control Ab (Bio X Cell, Rat IgG1) have been injected 1 day before and 1 day after the tumor inoculation (250 μl g/mouse/time point, i.p.).
Soluble CD25 Dosage
    sCD25 serum levels have been performed using the ELISA kit from Beckman Coulter (capture mAb: Clone 24204, detection Ab: clone 33b3) for cohorts 1 and 2, and by using Quantikine IL-2sRa from R&D Systems (capture mAb: clone 24204, detection Ab: clone MAB623) for cohorts 3 and 4. The experiments have been performed according to the manufacturers' instructions.
Quantitative RT-PCR:
    Tumor-bearing mice have been treated (or not) by 3 injections of anti-CTLA4 Ab as described above. Two days after the last injections, tumors have been harvested and digested into a cell suspension (5 mice/group). CD45 positive and negative fractions have been purified using anti-CD45 Ab coated magnetic beads (Miltenyi) followed by Automacs cell separation (Miltenyi) according to the manufacturer's instructions. RNAs have been extracted and retrotranscripted. Then a quantitative PCR has been performed using a Taqman procedure (Invitrogen). A commercial IL-15Ra probe (Applied Biosystems) has been used.

Flow Cytometry

Cells have been stained in PBS 2% FCS in presence of FcRBlocking and fluorochrome-coupled antibodies and viability marker for 15 min at 4° C. Then cells have been washed and resuspended in PBS for acquisition. For intracellular detection of cytokines, cells have been stimulated with PMA/ionomycin for 4 h in the presence of GolgiStop. After the membrane staining, cells have been permeabilized using the BD Cytofix/Cytoperm Kit (BD Biosciences) accordingly to the manufacturer's instructions. Samples have been acquired and analyzed on a FACSCanto II (BD Biosciences) using FACSDiva Software (BD Biosciences). All the antibodies (Anti-ICOSL, -LAG-3, -IFNg, -TNFa, -CD4, -CD3, -CD45) come from eBioscience. For viability, Vivid Yellow has been used (Molecular Probes).

Results

The Efficacy of Mouse Ipilimumab Relies on the IL-2R13/IL-2 Signaling Pathway and IL-15 and IL-2R Alpha Chain.

Two transplantable mouse tumor models syngeneic with C57BL/6 mice, i.e., MC38-OVA$^{dim}$ (colon cancer) and MCA205 sarcoma, were established for 10 days and then treated (when reaching a size of 40 mm$^2$) with systemic (i.v.) anti-CTLA4 antibodies (mouse Ipilimumab) every 3-4 days for 12 days. Tumor size was monitored until sacrifize. Ipilimumab mediated transient tumor control in both tumor models (FIG. 1A, FIG. 1B) in a CD4+ and CD8+ T cell-dependent manner, since antibodies depleting CD4 or CD8+ T cells abrogated Ipilimumab-mediated antitumor effects (not shown). The transcription profile of cytokine and cytokine receptor-encoding gene products revealed a markedly enhanced expression of IL-15Rα in both CD45+ and CD45– fractions of tumor beds post-anti-CTLA4 Ab (FIG. 2). The inventors then neutralize IL-15, IL-15 related cytokines (IL-2) and the corresponding receptors (CD25, CD122) during mouse Ipilimumab therapy using specific neutralizing antibodies directed against such molecules. Surprisingly neutralization of IL-2 and CD122 completely abolished the anti-CTLA4 Ab-mediated tumoricidal activity, in both MCA205 and MC38-OVA$^{dim}$ tumor models (FIG. 3A, 3B). Blockade of CD25 (IL-2Rα chain) prior to tumor inoculation and Ipilimumab therapy also reduced the antitumor effects of Ipilimumab (FIG. 4). Similarly, neutralization of rIL-15 using specific antibodies targeting this cytokine abolished Ipilimumab-induced tumor stabilization (FIG. 5).

Altogether, these data indicate that the efficacy of mouse Ipilimumab relies, at least in part, on the bioactivity of the IL-2/IL-2Rαβ signalling pathway.

Loss of ICOSL+CD4+ T Cells and Accumulation of Lag3+CD4+ T Cells in TILs of Responders.

The inventors investigated which T cell subsets accumulated in tumor beds post-Ipilimumab (after 3 injections), discriminating cancers responding from those progressing despite the treatment with anti-CTLA4 Abs. Flow cytometry analyses of the CD45+ fraction of tumor beds revealed that the efficacy of Ipilimumab relied upon the loss of ICOS ligand and the gain of Lag3 and TNFα/IFNγ-producing CD4+ T cells residing in regressing tumors (FIG. 6A, 6B, 6C).

There were no significant differences for IL-2-producing CD4+ T cells between the regressors and progressors (not shown).

The Combination of Mouse Ipilimumab and rIL-2 is Synergistic.

Since MCA205 sarcomas failed to respond to high doses of daily rIL-2 and were only partially sensitive to anti-CTLA4 Ab (transient and partial effect), the inventors combined anti-CTLA4 Ab (same protocol as described above) with rIL-2 (200,000 IU daily or 100,000 IU bid, daily). This combination therapy induced strong synergistic antitumor effects in 60% of mice (FIG. 7). These data suggest that tumor-bearing animals that failed to respond to anti-CTLA4 Ab because of a lack of bioactivity of IL-2 are advantageously compensated by a combination of both compounds.

In Metastatic Melanoma (MM), Low Basal sCD25 Serum Levels as Well as >1.5-Fold Increase of sCD25 after One Injection of 3-10 mg/kg of Anti-CTLA4 Ab/Human Ipilimumab Predict Clinical Benefit Observed at 4 Injections.

Since the bioactivity of IL-2 can be monitored by a serum surrogate marker of T cell activation, i.e., soluble CD25, the inventors undertook the dosing of sCD25 in the serum of metastatic melanoma (MM) patients included in a Phase II trial or treated on a compassionate basis with human Ipilimumab (3 or 10 mg/kg). They first analyzed, as a positive control, sCD25 in MM treated with rIL-2 at 1, 2, 5, and 9 million IU three times a week for 1 week using a first commercial ELISA kit revealing the normal ranges of sCD25 in normal volunteers and most MM (upper threshold of detection: 80 pMol/l, FIG. 8). In similar conditions, a second commercial ELISA kit revealed a value of 900 pg/ml (not shown). Therefore, to analyze the kinetics of the sCD25 rise in patients undergoing Ipilimumab therapy (FIGS. 8A, 8B and FIGS. 9A, 9B), the inventors defined the following criteria.

Criteria of response using the sCD25 kinetics: Basal levels of sCD25 should be in normal ranges (defined in normal volunteers, i.e., <80 pMol or 900 pg/ml) before Ipilimumab initiation and should increase, preferably by 1.5-fold, after one cycle of therapy.

Out of 28 MM, 7 partial responses (RECIST criteria) were recorded at cycle 4. Seven out 7 responded to the above-mentioned criteria. Out of the 21 non-responders (RECIST criteria), 8/28 were anticipated to respond (false positive). None of the patients whose sCD25 levels did not match the criteria of response developed a response (no false negatives) (Table 1).

TABLE 1

Prediction of clinical response and toxicity based on sCD25.

| Parameters | Prediction Test for Clinical Response sCD25 under threshold (<80 pM) AND Increase of sCD25 by 1.5 times post 1$^{st}$ Ipilimumab injection | Prediction Test for Toxicity sCD25 under threshold (<80 pM) AND Increase of sCD25 by 1.5 times post 2nd Ipilimumab injection |
|---|---|---|
| False Positive | 8/28 | 2/8 |
| False Negative | 0/28 | 0/8 |
| Correct Prediction | 20/28 | 6/8 |
| Sensitivity (%) | 100 | 100 |
| Specificity (%) | 61.9 | 33.33 |
| Predictive Positive Value (%) | 46.67 | 71.43 |
| Predictive Negative Value (%) | 100 | 100 |
| False Positive Rate (%) | 53.33 | 28.57 |
| False Negative Rate (%) | 0 | 0 |

To predict the efficacy, the sensitivity of the test (dosing of sCD25 in serum) was 100%, the specificity of the test was 61.9%, the positive predictive value (PPV) was 46.67%, the negative predictive value (NPV) was 100%, the false positive rate (FPR) was 53.33%, and the false negative rate (FNR) was 0%.

In Metastatic Melanoma (MM), Low Basal sCD25 Serum Levels as Well as >1.5-Fold Increase of sCD25 after Two Injections of 3-10 mg/kg of Anti-CTLA4 Ab/Human Ipilimumab Predict Toxicity Observed at 4 Injections.

Such a test could also predict toxicity but when used after 2 cycles of Ipilimumab: sensitivity=100%, specificity: 33.33%, PPV=71.43%, NPV=100%, FPR=28.57%, FNR=0%.

Out of 8 MM, 5 Ipilimumab-related toxicity were recorded at cycle 4. Five out of 5 responded to the above-mentioned criteria. Of the 3 patients that did not develop Ipilimumab-related toxicity, 2/3 were anticipated to undergo toxicity (false positive). None of the patients whose sCD25 levels did not match the criteria of toxicity developed toxicity (no false negatives) (Table 1).

Three patients developed severe Ipilimumab-related toxicity. Serum level of sCD25 increased continuously after each Ipilimuab injection (i.e., post-C2>post-C1>baseline; FIG. 10). Thus continuous sCD25 elevation after 2 injections predicts severe Ipilimumab-related toxicity (grade III-IV toxicities). None of the patients whose sCD25 level did not increase continuously developed toxicity.

In Metastatic Hormonoresistant Prostate Cancer, sCD25 Serum Levels Inversely Correlate with PSA Serum Levels.

In a series of 9 hormonoresistant prostate cancers treated for bone metastases with the combination of local radiotherapy and Ipilimumab at 10 mg/kg, sCD25 serum levels were inversely correlated with the PSA serum levels (surrogate marker of tumor burden) (FIG. 11, all 9 panels) in 7 out 9 cases. Interestingly, only one patient exhibited a spectacular complete response under Ipilimumab therapy and this patient, after initial Ipilimumab discontinuation attributed to a concomitant infection, showed a markedly enhanced rise in sCD25 after reintroduction of Ipilimumab (FIG. 12, showing all patients' kinetics of sCD25).

Example 3—High Serum Levels of Soluble CD25 Compromise the Efficacy of Anti-CTLA4 Blockade in Mice/High Soluble CD25 Serum Levels at Baseline are Associated with Resistance to Therapy in Metastatic Melanoma ("MM") Patients/Baseline sCD25 and Lactate Dehydrogenase (LDH) Serum Levels Predict Resistance to CTLA4 Blockade Materials & Methods Patients and Specimens.

The study was carried out on a total of 282 metastatic melanoma patients. Patient characteristics are depicted in Table 2 and Table 3. The immunomonitoring studies on fresh peripheral blood mononuclear cells (PBMC) were prospectively conducted on 10 patients. Patient samples (plasmas or sera) were provided by the Gustave Roussy Institute (Villejuif, France), the Memorial Sloan-Kettering Cancer Center (New York, USA), the Siena University Hospital (Siena, Italy), the German Cancer Research Center (Heidelberg, Germany), the Poznan University of Medical Sciences (Poznan, Poland) and the Essen University Hospital (Essen, Germany). Clinical responses were classified according to the Response Evaluation Criteria in Solid Tumors (RECIST) criteria and the immune-related response criteria IrRC.

Serum Levels of the Soluble Form of CD25 and LAG3.

Soluble CD25 (sCD25) and LAG3 (sLAG3) levels were determined by ELISA in accordance with the manufacturer's procedure. The Soluble IL-2 Receptor EIA Kit obtained from Beckman Coulter (Miami, Fla., USA) and the human soluble LAG3 Duo Set® from R&D Systems (Minneapolis, Minn., USA) were used for the sCD25 and sLAG3 dosage respectively. Patient sera (or plasmas) were collected before treatment and after the first and the second ipilimumab administrations. Mice: The mouse IL-2Rα Duo Set® from R&D Systems (Minneapolis, Minn., USA) was used for the sCD25 dosage.

Mice.

Mice aged between 7 and 12 weeks were used. Female C57BL/6J mice were obtained from Harlan (Gannat, France). Ifnar1 −/−C57BL/6J mice have been kindly provided by Gilles Uzé (UMR 5235, Montpellier Fance). Animals were maintained in specific pathogen-free conditions at either the Institut Gustave Roussy (IGR, Villejuif, France) or at the Peter MacCallum Cancer Center (East Melbourne, Australia) and housed in a temperature-controlled environment with a 12 h light-dark cycle and received food and water ad libitum. Experiments were carried out in compliance with French and European laws and regulations or with the Peter MacCallum Animal Experimentation Ethics Committee.

Cell Culture and Reagents.

OVA-expressing mouse fibrosarcoma MCA205 cells (class I MHC $H-2^b$, syngeneic with C57BL/6 mice) were cultured at 37° C. under 5% $CO_2$ in RPMI-1640 medium supplemented with 10% heat-inactivated fetal bovine serum (FBS), 100 units/ml penicillin G sodium, 100 μg/ml streptomycin sulfate, 2 mM L-glutamine, 1 mM sodium pyruvate and non-essential amino acids, all from Gibco-Invitrogen (Carlsbad, Calif., USA). OVA-expressing MCA205 cells selected in complete medium (as above) further supplemented with 50 μg/ml Hygromycin B (Invitrogen, Life Technologies™). Murine colon carcinoma MC38 $OVA^{dim}$ cells have been cultured in complete DMEM medium.

Tumor Challenge and Treatment.

Mice were subcutaneously injected in the right flank with $1 \times 10^6$ MCA205-OVA cells. When tumor sizes reached 25 to 40 $mm^2$, mice were injected intraperitoneally (i.p.) either with 100 μg of anti-CTLA4 (clone 9D9 (kindly supplied by J. Allison, University of Texas, MD Anderson, Houston, Tex.)) or with 100 μg of anti-PD1 (clone RMP1-14) from Bio X Cell (West Lebanon, N.H., USA). Anti-CTLA4 Ab was a mouse anti-mouse CTLA-4 antibody derived by immunization of human CTLA-4 transgenic mice (Peggs et al.). Mice were injected 5 times at 3-day intervals with 9D9 or 4 times at 4-day intervals with RMP1-14 and tumor sizes were routinely monitored by means of a common caliper until end-point reached.

Anti-CD122 (clone TM-beta1), anti-CD25 (clone PC-61.5.3), anti-IL10R (clone 1B1.3A), anti-LAG3 (clone C9B7W), anti-ICOS (clone 17G9), and rat IgG (LTF-2, HRPN) used in vivo were obtained from Bio X Cell and anti-IL-2 (JES6-1A12) and anti-IL-15 (AIO.3) were provided by eBioscience (San Diego, Calif., USA). Mice received 200 μg of anti-CD122, 250 μg of anti-CD25, 500 μg of anti-IL-10R, 200 μg of anti-LAG3, and 250 μg of anti-ICOS, injected i.p. 1 day before each injection. Anti-IL-15 and anti-IL-2 were administered into the tumor bed at 20 μg on day 0 and day 3 and 10 μg per mouse on day 6 post-anti-CTLA4. sCD25 (Recombinant Human IL-2 Receptor a, Peprotech, Rocky Hill, N.J., USA) was injected i.v. at 25 μg as described in FIG. 13e).

Flow Cytometry.

Mice: Eight-color flow cytometry analysis was performed with fluorescein isothiocyanate, phycoerythrin, phycoerythrin cyanin 7, Peridinin Chlorophyll Protein Cyanin 5.5, allophycocyanin cyanin 7, Pacific blue, and allophycocyanin-conjugated antibodies. The staining was performed on spleens and tumors dissected from mice two days after the third injection of anti-CTLA4. Briefly, excised tumors were cut in small pieces and digested in RPMI medium containing Liberase™ at 25 μg/ml (Roche) and DNase I at 150 UI/ml (Roche) for 30 minutes at 37° C. Single-cell suspension was obtained by crushing the pieces on a 100 μm cell strainer. Two million splenocytes (after red blood cell lysis) or tumor cells were preincubated with purified anti-mouse CD16/CD32 (clone 93, purchased from eBioscience) for 15 minutes at 4° C. before the membrane staining. For intracellular staining, the FoxP3 staining kit (eBioscience) was used according to the manufacturer's instructions. Dead cells were excluded using the Live/Dead Fixable Yellow dead cell stain kit (Life Technologies™). Stained samples were run on a Canto II (BD Biosciences, San Jose, Calif., USA) cytometer and analyses were performed with FlowJo software (Tree Star, Ashland, Oreg., USA). For cytokine staining, cells were stimulated for 4 hours at 37° C. with 50 ng/ml of phorbol 12-myristate 13-acetate (PMA), 1 μg/ml of ionomycin (Calbiochem) and BD Golgi STOP™ (BD Biosciences) according to the manufacturers' instructions. Anti-CD45.2 (104), CD127 (A7R34), FoxP3 (FJK-16s), LAG3 (eBioC9B7W), ICOS (7E17G9), ICOSL (HK5.3), IL17a (eBio17B7), IFN-γ (XMG1.2), and TNF-α (MP6-XT22) and isotype controls rat IgG1 (eBRG1), IgG2a (eBRG2a), and IgG2b (eBRG2b) were purchased from eBioscience. Anti-CD3 (145-2C11), CD25 (PC61.5.3), IL-10 (554467), CD11b (M1/70), and rat IgG1κ were provided by BD Biosciences. Anti-CD4 (GK1.5), CD8β (YTS1567.7), CD11c (N418), and rat IgG2a (RTK2758) were purchased from BioLegend (San Diego, Calif., USA). Anti-CD25 (7D4) was provided by Miltenyi Biotech. Human: Anti-CD3 (BW262/56) and mouse IgG1 (I55-21F5) were purchased from Miltenyi Biotech. Anti-CD4 (SK3), CD8 (SK1), CD25 (M-A251), CD45 (J33), and mouse IgG1 (MOPC-21) were provided by BD Biosciences. Anti-Foxp3 (PCH101) was purchased from eBioscience and anti-LAG3 from R&D Systems.

Bioinformatics and statistical analysis. Data were analyzed with Microsoft Excel (Microsoft Co., Redmont, Wash., USA), Prism 5 (GraphPad, San Diego, Calif., USA) and the environment R (R Foundation for Statistical Computing, Vienna, Austria). Data are presented as mean±SEM and p-values were computed by paired or unpaired t-test where applicable. Tumor growth modeling was carried out with linear mixed effect modeling on log pre-processed tumor volumes (Sugar et al.). Reported p-values are obtained from testing jointly that both tumor growth slopes and intercepts (on log scale) are the same between treatment groups of interest. Overall survivals (OS) determined from the first injection and immune-related Response Criteria (ir-RC) at the date of diagnosis/time of treatment were used as the primary end-points. Likelihood ratio test (LRT) from Cox proportional hazards regression modeling was used for assessing predictors of survival (including patient characteristics) as well as the added prognostic value of sCD25. All reported tests are two-tailed and were considered significant for p-value<0.05. Regression model analyses were conducted on the log basis 2 transformed marker concentration and were evaluated with the use of Schoenfeld residuals. Therefore, hazard ratios and associated 95% confidence intervals are easily interpretable in terms of doubling in concentration. For graphical representations, serum marker levels were partitioned into 2/3 groups based on the observed median/tertile (sCD25, sLAG3) or a threshold of 250 (LDH). For completeness, statistics from both specifications of the marker in the model are presented but statistics resulting from the marker(s) in the continuous scale are used to draw conclusions.

TABLE 2

Characteristics of Patients Ipilimumab treatment

|  |  |  | n (%) | Overall Survival Univariate Analsysis HR [95% CI], p value |
|---|---|---|---|---|
| Nb of patients |  |  | 262 |  |
| Median Survival Time | Weeks |  | 41 (3-156) |  |
| Age | Mean (Min-Max) |  | 59.78 [16.37; 91.05] |  |
| Gender |  | Male | 128 (59.8) | 1 |
|  |  | Female | 86 (40.2) | 0.90 [0.63; 1.28], p < 0.5501 |
| Metastasis |  | M1a | 29 (14.9) | 1 |
|  |  | M1b | 35 (18) | 1.99 [0.88; 4.51], p < 0.099 |
|  |  | M1c | 130 (67) | 5.22 [2.52; 10.82], p << 1e−04 |
| Nb of |  | 1 | 7 (4.6) | 1 |
| Ipilimumab |  | 2 | 18 (11.8) | 0.21 [0.08; 0.59], p < 0.0027 |
| Injection |  | 3 | 21 (13.7) | 0.27 [0.10; 0.72], p < 0.0087 |
|  |  | 4 | 101 (66) | 0.13 [0.05; 0.32], p << 1e−04 |
|  |  | >4 | 6 (3.9) | NA |
| Dose of |  | 3 mg/kg | 204 (77.9) | 1 |
| Ipilimumab |  | 10 mg/kg | 16 (6.1) | 0.10 [0.01; 0.77], p < 0.0271 |
|  |  | 3 or 10 (Blinded) | 42 (14) |  |
| Clinical | RECIST | CR | 6 (3.3) | 1 |
| response |  | PR | 21 (11.7) | 1 |
|  |  | SD | 17 (9.4) | 2.83 [0.47; 17.22], p < 0.2585 |
|  |  | PD | 136 (75.6) | 20.18 [4.87; 83.70], p << 1e−04 |
|  |  | Unknown | 29 (14) |  |
|  | IrRC | CR | 4 (2.9) | 1 |
|  |  | PR | 22 (15.7) | 1 |
|  |  | SD | 26 (18.6) | 4.35 [0.91; 20.73], p < 0.0646 |
|  |  | PD | 88 (62.9) | 23.50 [5.66; 97.52], p << 1e−04 |
|  |  | Unknown | 10 (7) |  |

TABLE 2-continued

Characteristics of Patients Ipilimumab treatment

|  |  |  | n (%) | Overall Survival Univariate Analsysis HR [95% CI], p value |
|---|---|---|---|---|
| Toxicity |  | Grade 0 | 100 (64.1) | 1 |
|  |  | Grade I-II | 44 (28.2) | 0.41 [0.23; 0.73], p < 0.0027 |
|  |  | Grade III-IV | 12 (7.7) | 0.39 [0.14; 1.10], p < 0.0759 |
| Line of |  | 1 | 50 (21) |  |
| Ipilimumab |  | 2 | 130 (55) |  |
| Treatment |  | 3 | 36 (15) |  |
|  |  | 4 | 20 (8) |  |
|  |  | 5 | 1 (0.5) |  |
| LDH at | IU | <250 | 104 (41.8) | 1 |
| Baseline |  | 250-500 | 94 (37.8) | 2.47 [1.68; 3.62], p << 1e-04 |
|  |  | >500 | 51 (20.5) | 5.08 [3.25; 7.95], p << 1e-04 |
| sCD25 at | pg/ml | <1260 (Low) | 130 (49.6) | 1 |
| baseline |  | >1260 (High) | 132 (50.4) | 1.39 [1.02; 1.90], p < 0.0346 |
| sLAG3 at | pg/ml | <849 (Low) | 96 (49.5) | 1 |
| baseline |  | >849 (High) | 98 (50.5) | 1.21 [0.84; 1.75], p < 0.3093 |

Table 2 summarizes the characteristics of the patients. Hazard ratios were estimated with the use of unstratified Cox proportional hazards models. Lines represent 95% confidence. The metastasis (M) stage was classified according to the tumor-node-metastasis (TNM) categorization for melanoma. LDH, Lactate dehydrogenase. IU: International Unit.

dosage of rIL-2 (Saadoun et al.), MM patients (N=262) being administered ipilimumab (most of them receiving 3 mg/kg on a compassionate basis, Table 2) exhibited a significant rise in the serum levels of sCD25 (FIG. 13 a-b). Intriguingly, a proportion of MM patients presented with high baseline levels of sCD25 (above the median of normal volunteers: 330-1650 pg/ml (Bien, E. & Balcerska, A.)), a

TABLE 3

Characteristics of Patients Tremelimumab treatment

|  |  |  | n (%) | Overall Survival Univariate Analsysis HR [95% CI], p value |
|---|---|---|---|---|
| Nb of patients |  |  | 20 |  |
| Median Survival Time | Weeks (Min-Max) |  | 32 [12; 132] |  |
| Age | Mean (Min-Max) |  | 56.55 [27; 81] | 0.99 [0.95; 1.03], p < 0.6822 |
| Gender |  | Male | 16 (80) | 1 |
|  |  | Female | 4 (20) | 0.39 [0.07; 2.26], p < 0.2167 |
| Metastasis |  | M1a | 10 (50) | 1 |
|  |  | M1b | 4 (20) | 2.46 [0.61; 9.95], p < 0.2053 |
|  |  | M1c | 6 (30) | 0.97 [0.27; 3.47], p < 0.9649 |
| Nb of |  | 1 | 12 (60) | 1 |
| Tremelimumab |  | 2 | 4 (20) | 0.21 [0.03; 1.38], p < 0.0386 |
| Injection |  | 3 | 3 (15) | 0.33 [0.05; 2.09], p < 0.1498 |
|  |  | 4 | 1 (5) | 0.8 [0.12; 5.19], p < 0.7971 |
| Clinical | RECIST | CR | 3 (15) | 1 |
| response |  | PD | 17 (85) | 8.18 [0.43; 155.99], p < 0.0403 |
| Toxicity |  | No Toxicity | 8 (40) | 1 |
|  |  | Toxicity | 12 (60) | 0.39 [0.13; 1.18], p < 0.0867 |
| LDH at |  | Normal | 11 (55) | 1 |
| Baseline |  | High | 9 (45) | 6.76 [1.97; 23.23], p < 0.0011 |
| sCD25 at | pg/ml | <490 (Low) | 10 (50) | 1 |
| baseline |  | >490 (High) | 10 (50) | 1.58 [0.52; 4.82], p < 0.3999 |
| sCD25 | pg/ml | <921 (Low) | 10 (50) | 1 |
| Post C1 |  | >921 (High) | 10 (50) | 1.88 [0.62; 5.74], p < 0.2440 |

Table 3 summarizes the characteristics of the patients. Hazard ratios were estimated with the use of unstratified Cox proportional hazards models. Lines represent 95% confidence. The metastasis (M) stage was classified according to the tumor-node-metastasis (TNM) categorization for melanoma. LDH, Lactate dehydrogenase.

Results

Soluble CD25 Inhibits the Efficacy of Ipilimumab

The inventors monitored surrogate markers of lymphocyte activation such as soluble CD25 and Lag3 in the serum of cancer patients (MM) treated with ipilimumab. Like patients harbouring autoimmune vasculitis receiving a low finding reminiscent of the high IL-2/IL-10 ratio found in circulating $CD4^+$ T cells (data not shown). Of note, the concentrations of sLAG3 were barely augmented post-ipilimumab or post-rIL-2 (FIG. 13 c-d).

To investigate the negative impact of high sCD25 baseline levels on the efficacy of anti-CTLA4 blockade, the inventors experimentally raised the serum concentrations of sCD25 by iterative systemic infusions of high doses of recombinant sCD25 in mice during ipilimumab administrations (FIG. 13e, left panel). Indeed, it is noteworthy that mouse ipilimumab failed to induce shedding of sCD25 at this dose/scheduling, in contrast to human settings (FIG. 13a, FIG.

14a). This maneuver significantly compromised the antitumor effects observed right after starting CTLA4 blockade (FIG. 13e, right panel and FIG. 14b). In the presence of high concentrations of soluble CD25, the ipilimumab-induced influx of CD45$^+$ leukocytes and the downregulation of Foxp3 and ICOS expression on CD4$^+$Lag3$^+$ TILs associated with tumor regression were significantly impaired (FIG. 14 c-d, FIG. 13 f-g) while CD8$^+$ ICOS$^+$TILs that were CD122-independent were not affected by sCD25 (FIG. 14d).

Altogether, these preclinical data indicate that high concentrations of the receptor sCD25 in the serum prior to therapy are detrimental for the efficacy of a CTLA4 blockade immunotherapy.

Soluble CD25 Inhibits the Efficacy of Tremelimumab

MM patients (N=20) (Table 3) treated with an alternative anti-CTLA-4 mAb, Tremelimumab (3 weeks after a single dose of 15 mg/kg) exhibited a significant rise in the serum levels of sCD25 (FIG. 15).

Baseline sCD25 and LDH Serum Levels Predict Resistance to CTLA4 Blockade Immunotherapy The inventors analyzed the potential negative impact of high baseline levels of sCD25 on the clinical outcome of metastatic melanoma ("MM") patients receiving ipilimumab in a retrospective study encompassing 9 independent cohorts from 5 different countries (Table 2). Considering the median value of sCD25 in the whole cohort of 262 patients, they showed that sCD25 as well as LDH levels, immune-related response criteria (irRC) at 4 weeks, and M1a/1b/1c dissemination status were all parameters statistically associated with overall survival (OS) in univariate analyses (Table 2, FIG. 16, HR=1.29 [1.06; 1.57], p<0.00827, FIG. 17 a-b, focus on distinct cohorts in FIG. 18a) whereas levels of sLAG3 and lymphocyte counts at diagnosis did not correlate with OS (HRc=1.02 [0.94; 1.11], p<0.65, FIG. 18b and not shown). The prognostic value of sCD25 remained significant (HR=1.26 [1.04; 1.54], p<0.0165) after including LDH in the model pointing to an independent contribution of sCD25 to the OS (FIG. 17c). sCD25 basal concentrations above a reference expression level at diagnosis correlated with poor outcomes for patients thereafter treated with ipilimumab, specifically in the subset presenting with high basal LDH levels, i.e., above about 500 IU (FIG. 17c). Similarly, sCD25 levels above a reference expression level at 3 weeks (T21) post-ipilimumab negatively predicted OS (FIG. 17d) while the ratio between sCD25 at T21/T0 failed to do so (FIG. 18c). The inventors conclude from their experiments that combined with LDH values, the basal sCD25 serum level represents a valuable predictor of resistance to ipilimumab or Tremelimumab.

The inventors analyzed the potential negative impact of levels of sCD25 above a reference expression level on the clinical outcomes of MM patients receiving Tremelimumab (another anti-CTLA4 Ab, MedImmune) in a retrospective study (FIG. 19, Table 3). Considering the continuous value of sCD25 in the cohort of 20 patients, the inventors show that sCD25 has the same trend of association with overall survival (OS) in univariate analysis (2.03 [0.77; 5.36], p<0.1503). LDH at baseline (i.e., before any treatment) and RECIST criteria were statistically associated with overall survival (OS) in univariate analysis (Table 3).

CONCLUSIONS

Both preclinical (FIG. 13e) and clinical data (FIG. 17 a-b) indicate that the antitumor efficacy of anti-CTLA4 blockade immunotherapy is compromised in patients presenting with basal serum levels of sCD25 above a reference expression level at diagnosis. In MM presenting with LDH>500 IU, sCD25 serum concentration added a negative prognostic value, indicating a subset of about 25% patients doomed to fail ipilimumab therapy (FIG. 17c).

Detecting high sCD25 basal concentrations at diagnosis is an indication to use humanized anti-CD25 therapeutic strategies (radioimmunoconjugates of anti-CD25 and immunotoxins) in MM prior to ipilimumab therapy.

REFERENCES

Kaehler K C, Piel S, Livingstone E, Schilling B, Hauschild A, Schadendorf D. Update on immunologic therapy with anti-CTLA-4 antibodies in melanoma: identification of clinical and biological response patterns, immune-related adverse events, and their management. Semin. Oncol. 2010 October; 37(5):485-98.

Hodi F S, O'Day S J, McDermott D F, Weber R W, Sosman J A, Haanen J B, et al. Improved survival with Ipilimumab in patients with metastatic melanoma. N. Engl. J. Med. 2010 Aug. 19; 363(8):711-23.

Robert C, Thomas L, Bondarenko I, O'Day S, Weber J, Garbe C, et al. Ipilimumab plus dacarbazine for previously untreated metastatic melanoma. N. Engl. J. Med. 2011 Jun. 30; 364(26):2517-26.

Weber J. Ipilimumab: controversies in its development, utility and autoimmune adverse events. Cancer Immunol. Immunother. 2009 May; 58(5): 823-30.

Di Giacomo A M, Biagioli M, Maio M. The emerging toxicity profiles of anti-CTLA-4 antibodies across clinical indications. Semin. Oncol. 2010 October; 37(5):499-507.

Wolchok J D, Neyns B, Linette G, Negrier S, Lutzky J, Thomas L, et al. Ipilimumab monotherapy in patients with pretreated advanced melanoma: a randomised, double-blind, multicentre, phase 2, dose-ranging study. Lancet Oncol. 2010 February; 11(2):155-64.

Weber J S, Kahler K C, Hauschild A. Management of Immune-Related Adverse Events and Kinetics of Response With Ipilimumab. Journal of Clinical Oncology. 2012 May 21; 30(21):2691-7.

Wolchok J D, Hoos A, O'Day S, Weber J S, Hamid O, Lebbé C, et al. Guidelines for the evaluation of immune therapy activity in solid tumors: immune-related response criteria. Clin. Cancer Res. 2009 Dec. 1; 15(23):7412-20.

Peggs, K. S., Quezada, S. A., Chambers, C. A., Korman, A. J. & Allison, J. P. Blockade of CTLA-4 on both effector and regulatory T cell compartments contributes to the antitumor activity of anti-CTLA-4 antibodies. *J Exp Med* 206, 1717-1725 (2009).

Sugar, E., Pascoe, A. J. & Azad, N. Reporting of preclinical tumor-graft cancer therapeutic studies. *Cancer Biol Ther* 13, 1262-1268 (2012).

Hodi, F. S., et al. Improved survival with ipilimumab in patients with metastatic melanoma. *N Engl J Med* 363, 711-723 (2010).

Robert, C., et al. Ipilimumab plus dacarbazine for previously untreated metastatic melanoma. *N Engl J Med* 364, 2517-2526 (2011).

Topalian, S. L., et al. Safety, activity, and immune correlates of anti-PD-1 antibody in cancer. *N Engl J Med* 366, 2443-2454 (2012).

Saadoun, D., et al. Regulatory T-cell responses to low-dose interleukin-2 in HCV-induced vasculitis. *N Engl J Med* 365, 2067-2077 (2011).

Bien, E. & Balcerska, A. Serum soluble interleukin 2 receptor alpha in human cancer of adults and children: a review. *Biomarkers* 13, 1-26 (2008).

Ribas, A., et al. Phase III randomized clinical trial comparing tremelimumab with standard-of-care chemotherapy in patients with advanced melanoma. *J Clin Oncol* 31, 616-622 (2013).

The invention claimed is:

1. An in vitro method of assessing the sensitivity of a subject having melanoma to an immunotherapeutic molecule acting on the subject's T cells for treating melanoma, which method comprises a step a) of determining, in a biological sample from said subject selected from a blood, a serum, a plasma sample or a derivative thereof, the respective basal expression levels of soluble CD25 (sCD25) and of lactic acid dehydrogenase (LDH), and, when the sCD25 and LDH expression levels are determined, a step b) of comparing said sCD25 and LDH basal levels of expression to sCD25 and LDH, respectively, thereby assessing whether the subject having a tumor is sensitive or resistant to the immunotherapeutic molecule, wherein the immunotherapeutic molecule is an anti-CTLA-4 antibody and:

when the LDH reference expression level is about 500 IU, the step of assessing whether the subject having melanoma is sensitive or resistant to the immunotherapeutic molecule comprises:
i) identifying the subject as having melanoma that is resistant to the immunotherapeutic molecule based on the sCD25 basal expression level being above the sCD25 reference expression level and/or the LDH basal expression level being above the LDH reference expression level of about 500 IU; or
ii) identifying the subject as having melanoma that is sensitive to the immunotherapeutic molecule based on the sCD25 basal expression level being below the sCD25 reference expression level together with the LDH basal expression level being below the LDH reference expression level of about 500 IU; and
iii) administering therapeutic doses of an anti-CTLA-4 antibody to the subject identified as having a melanoma that is sensitive to the immunotherapeutic molecule, or
iv) administering therapeutic doses of an anti-CTLA-4 antibody in combination with therapeutic doses of a compensatory molecule selected from interleukin-2 (IL-2), interleukin-15 (IL-15), IL-2 superkine, sushi IL-15, radioimmunoconjugate of anti-CD25 and immunotoxin or a combination of the compensatory molecules to the subject identified as having a melanoma that is resistant to the immunotherapeutic molecule.

2. The method according to claim 1, wherein the sCD25 and LDH expression levels determined in step a) are the sCD25 and LDH basal expression levels in the subject, and wherein step b) further comprises comparing said sCD25 and LDH basal expression levels, used as reference expression levels, to sCD25 and LDH response expression levels in the subject determined after administration to said subject of the immunotherapeutic molecule.

3. The method according to claim 1, wherein the melanoma is a metastatic or an unresectable melanoma.

4. The method according to claim 2, wherein the method comprises a step a) of determining the sCD25 and LDH basal expression levels, in a biological sample of the subject having melanoma, before any administration to the subject of the immunotherapeutic molecule for treating the subject's melanoma, a step a') of determining, in a biological sample of the subject having melanoma, the respective sCD25 and LDH response expression levels after the administration to said subject of at least one therapeutic dose of the immunotherapeutic molecule for treating melanoma, and a step b) of comparing said sCD25 and LDH response expression levels to said sCD25 and LDH basal expression levels and to reference expression levels in a control population, a sCD25 response expression level identical to the sCD25 basal expression level or below the sCD25 reference expression level, together with a LDH basal expression level below the LDH basal expression level and reference expression level being indicative of the sensitivity of the subject to the immunotherapeutic molecule.

5. The method according to claim 2, wherein the method comprises a step a) of determining the sCD25 and LDH basal expression levels, in a biological sample of the subject having melanoma, before any administration to the subject of the immunotherapeutic molecule for treating the subject's melanoma, a step a') of determining, in a biological sample of the subject having a tumor, the respective sCD25 and LDH response expression levels after the administration to said subject of at least one therapeutic dose of the immunotherapeutic molecule for treating melanoma, and a step b) of comparing said sCD25 and LDH response expression levels to said sCD25 and LDH basal expression levels and to reference expression levels in a control population, a sCD25 response expression level above the sCD25 basal expression level or the reference expression level, together with a LDH basal expression level above the LDH basal expression level and reference expression level, being indicative of a resistance of the subject to the immunotherapeutic molecule.

6. The method according to claim 1, wherein the LDH reference expression level is about 500 IU and the sCD25 reference expression level is 1260 pg/ml, and wherein the step of assessing whether the subject having the tumor is sensitive or resistant to the immunotherapeutic molecule comprises:
i) identifying the subject as having the tumor that is resistant to the immunotherapeutic molecule based on the sCD25 basal expression level being above the sCD25 reference expression level of 1260 pg/ml and/or the LDH basal expression level being above the LDH reference expression level of about 500 IU; or
ii) identifying the subject as having the tumor that is sensitive to the immunotherapeutic molecule based on the sCD25 basal expression level being below the sCD25 reference expression level of 1260 pg/ml and the LDH basal expression level being below the LDH reference expression level of about 500 IU.

7. The method of claim 1, the method comprising administering therapeutic doses of an anti-CTLA-4 antibody to the subject identified as having a melanoma that is sensitive to the immunotherapeutic molecule.

8. The method of claim 7, wherein the anti-CTLA-4 antibody is Ipilimumab or Tremelimumab.

9. A method of treating a melanoma in a subject, the method comprising the steps of:
a) determining, in a biological sample from said subject selected from a blood, a serum, a plasma sample or a derivative thereof, the basal expression levels for sCD25 and LDH;
b) comparing said basal expression levels of sCD25 and LDH in the biological sample of the subject to reference expression levels for sCD25 and LDH; and
c) treating a melanoma in the subject by administering to the subject:
i) therapeutic doses of an anti-CTLA-4 antibody alone when the basal expression level of sCD25 in the biological sample of the subject is below the reference expression level for sCD25 of 1260 pg/ml and the basal expression level of LDH in the biological sample of the subject is below the reference expression level for LDH of about 500 IU, or ii) therapeutic doses of an anti-CTLA-4 antibody in combination with therapeutic doses of a compensatory molecule selected from interleukin-2 (IL-2), interleukin-15 (IL-15), IL-2 superkine, sushi IL-15, radioimmunoconjugate of anti-CD25 and immunotoxin or a combination of the compensatory molecules when the expression level of sCD25 in the biological sample of the subject is above the reference expression level for sCD25 of 1260 pg/ml and/or the expression level of LDH in the biological sample of the subject is above the reference expression level for LDH of about 500 IU.

10. The method of claim 9, wherein the anti-CTLA-4 antibody is Ipilimumab or Tremelimumab.

11. The method of claim 1, said method comprising administering therapeutic doses of an anti-CTLA-4 antibody in combination with therapeutic doses of a compensatory molecule selected from interleukin-2 (IL-2), interleukin-15 (IL-15), IL-2 superkine, sushi IL-15, radioimmunoconjugate of anti-CD25 and immunotoxin or a combination of the compensatory molecules to the subject identified as having a melanoma that is resistant to the immunotherapeutic molecule.

12. The method of claim 7, wherein the anti-CTLA-4 antibody is Ipilimumab or Tremelimumab.

* * * * *

UNITED STATES PATENT AND TRADEMARK OFFICE
CERTIFICATE OF CORRECTION

PATENT NO. : 9,810,692 B2  
APPLICATION NO. : 14/438275  
DATED : November 7, 2017  
INVENTOR(S) : Dalil Hannani et al.

Page 1 of 1

It is certified that error appears in the above-identified patent and that said Letters Patent is hereby corrected as shown below:

In the Specification

Column 18,  
Lines 51-52, "250 μlg/mouse/time point, i.p.)." should read --250 μg/mouse/time point, i.p.).--.

Column 24,  
Line 2, "(I55-21F5)" should read --(IS5-21F5)--.

Signed and Sealed this  
Third Day of July, 2018

Andrei Iancu  
*Director of the United States Patent and Trademark Office*